United States Patent
Campanella

(10) Patent No.: US 11,118,227 B2
(45) Date of Patent: Sep. 14, 2021

(54) METHODS OF IDENTIFYING AGENTS HAVING NEUROPROTECTIVE OR ANTI-OXIDANT ACTIVITY FOR REGULATING MITOCHONDRIAL FUNCTION

(71) Applicant: THE ROYAL VETERINARY COLLEGE, London (GB)

(72) Inventor: Michelangelo Campanella, London (GB)

(73) Assignee: The Royal Veterinary College, London (GB)

(*) Notice: Subject to any disclaimer, the term of this patent is extended or adjusted under 35 U.S.C. 154(b) by 0 days.

(21) Appl. No.: 15/745,466

(22) PCT Filed: Jul. 18, 2016

(86) PCT No.: PCT/GB2016/052169
§ 371 (c)(1),
(2) Date: Jan. 17, 2018

(87) PCT Pub. No.: WO2017/013416
PCT Pub. Date: Jan. 26, 2017

(65) Prior Publication Data
US 2018/0208986 A1 Jul. 26, 2018

(30) Foreign Application Priority Data
Jul. 17, 2015 (GB) ..................... 1512609

(51) Int. Cl.
*C12Q 1/68* (2018.01)
*C12Q 1/6883* (2018.01)
*C12Q 1/686* (2018.01)

(52) U.S. Cl.
CPC .......... *C12Q 1/6883* (2013.01); *C12Q 1/686* (2013.01); *C12Q 2600/136* (2013.01); *C12Q 2600/158* (2013.01)

(58) Field of Classification Search
None
See application file for complete search history.

(56) References Cited

FOREIGN PATENT DOCUMENTS

| WO | WO 2012/037547 | 3/2012 | |
|---|---|---|---|
| WO | WO 2014/138791 | 9/2014 | |
| WO | WO-2014138791 A1 * | 9/2014 | ........... A61K 31/437 |

OTHER PUBLICATIONS

Lerner et al. Aging Cell vol. 12, pp. 966-977 (Year: 2013).*
Chelli et al., "PK 11195 Differentially Affects Cell Survival in Human Wild-Type and 18 kDa Translocator Protein-Silenced ADF Astrocytoma Cells", *J Cellular Biochemistry* 105:712-723, 2008.
Gatliff et al., "TSPO Interacts with VDAC1 and Triggers a ROS-Mediated Inhibition of Mitochondrial Quality Control", *Autophagy* 10(12):2279-2296, 2014.
Gatliff et al., "TSPO is a REDOX Regulator of Cell Mitophagy", *Biochemical Society Transactions* 43:543-552, 2015.
Papadopoulos et al., "Translocator Protein (18 kDa) TSPO: An Emerging Therapeutic Target in Neurotrauma", *Experimental Neurology* 219:53-57, 2009.
Park et al., "PF-4708671, A Specific Inhibitor of p70 Ribosomal S6 Kinase 1, Activates Nrf2 by Promoting p62-Dependent Autophagic Degradation of Keap1", *Biochemical and Biophysical Research* 466:499-504, 2015.
Rao et al., "The Antioxidant Transcription Factor Nrf2 Negatively Regulates Autophagy and Growth Arrest Induced by the Anticancer Redox Agent Mitoquinone", *J Biological Chemistry* 285:34447-34459, 2010.
Uruno et al, "The Keap1Nrf2 System as Ansensor for Electophiles", *Nitric Oxide* 25:153-160, 2011.
PCT Search Report and Written Opinion for PCT/GB2016/052169 dated Oct. 26, 2016 (11 pages).
Chen P-C et al. Proc Nat Acad Sci USA, 2009 Nrf2-mediated neuroprotection in the MPTP mouse model of Parkinson's disease: Critical role for the astrocyte. 106(8):2933-2938.
Cheng et al. Impaired redox signaling and antioxidant gene expression in endothelial cells in diabetes: a role for mitochondria and the nuclear factor-E2-related factor 2-Kelch-like ECH-associated protein 1 defense pathway. Antioxid. Redox Signal. 2011;14:469-487.
De Castro et al. Mitochondrial quality control and neurological disease: an emerging connection. Expert Rev. Mol. Med. 2010;12:e12.
Deas et al. 2011. Mitophagy and Parkinson's disease: The PINK1-parkin link. Biochim Biophys Acta. 1813(4):623-633.
Ding and Yin. Mitophagy: mechanisms, pathophysiological roles, and analysis. Biol. Chem. 2012;393:547-564.
East et al. PMI: a novel, ΔΨm independent, Mitophagy Inducer. Chem Biol. Nov. 20, 2014;21(11):1585-96.
Feng et al (2014) J Nucl Med. Dec. 2014;55(12):1966-72. doi: 10.2967/jnumed.114.143727. Epub Nov. 13, 2014. In vivo quantification of cerebral translocator protein binding in humans using 6-chloro-2-(4'-123I-iodophenyl)-3-(N,N-diethyl)-imidazo[1,2-a]pyridine-3-acetamide SPECT.
Fu et al. Regulation of mitophagy by the Gp78 E3 ubiquitin ligase. Mol. Biol. Cell. 2013;24:1153-1162.
Geisler et al. PINK1/Parkin-mediated mitophagy is dependent on VDAC1 and p62/SQSTM1. Nat. Cell Biol. 2010;12:119-131.
Hayes et al. Cancer chemoprevention mechanisms mediated through the Keap 1-Nrf2 pathway. Antioxid. Redox Signal. 2010;13:1713-1748.
Higgins and Coughlan 2014 Br J Pharmacol 171:1917-42.

(Continued)

*Primary Examiner* — Celine X Qian
(74) *Attorney, Agent, or Firm* — Mueting Raasch Group

(57) ABSTRACT

A method for assessing whether a test substance or treatment is potentially neuroprotective or anti-oxidant, the method comprising the steps of exposing a cell to the test substance or treatment assessing the TSPO level in the cell, wherein a substance or treatment is considered to be potentially anti-oxidant and/or neuroprotective if the TSPO level is decreased. The method may comprise the step of assessing the level of mitophagy in the cell, wherein a substance or treatment is considered to be anti-oxidant or neuroprotective if the level or induction of mitophagy is increased and the TSPO level is decreased.

13 Claims, 18 Drawing Sheets

(56) References Cited

OTHER PUBLICATIONS

Hirota et al. 2015. Mitophagy is primarily due to alternative autophagy and requires the MAPK1 and MAPK14 signaling pathways. Autophagy. 11(2):332-43.
Hong et al. The role of Nrf2 signaling in the regulation of antioxidants and detoxifying enzymes after traumatic brain injury in rats and mice. Acta Pharmacol. Sin. 2010;31:1421-1430.
Ishii et al. Transcription factor Nrf2 coordinately regulates a group of oxidative stress-inducible genes in macrophages. J. Biol. Chem. 2000;275:16023-16029.
Jain et al. p62/SQSTM1 is a target gene for transcription factor NRF2 and creates a positive feedback loop by inducing antioxidant response element-driven gene transcription. J. Biol. Chem. 2010;285:22576-22591.
Jin et al. Mitochondrial membrane potential regulates PINK1 import and proteolytic destabilization by PARL. J. Cell Biol. 2010;191:933-942.
Kamat et al 2014 Cell Biochemistry and Biophysics 70: 707-719.
Karbowski and Neutzner. Neurodegeneration as a consequence of failed mitochondrial maintenance. Acta Neuropathol. 2012;123:157-171.
Kensler et al. Cell survival responses to environmental stresses via the Keap1-Nrf2-ARE pathway. Annu. Rev. Pharmacol. Toxicol. 2007;47:89-116.
Kensler et al. Keap1-nrf2 signaling: a target for cancer prevention by sulforaphane. Top. Curr. Chem. 2013;329:163-177.
Kim et al. Selective degradation of mitochondria by mitophagy. Arch. Biochem. Biophys. 2007;462:245-253.
Lau et al. A noncanonical mechanism of Nrf2 activation by autophagy deficiency: direct interaction between Keap1 and p62. Mol. Cell. Biol. 2010;30:3275-3285.
Liu et al. Mitochondrial outer-membrane protein FUNDC1 mediates hypoxia-induced mitophagy in mammalian cells. Nat. Cell Biol. 2012;14:177-185.
Lokireddy et al. The ubiquitin ligase Mul1 induces mitophagy in skeletal muscle in response to muscle-wasting stimuli. Cell Metab. 2012;16:613-624.
Matic et al. Controlled and impaired Mitochondrial Quality in neurons: Molecular Physiology and Prospective Pharmacology. Pharmacological Research in press.
Narendra and Youle. Targeting mitochondrial dysfunction: role for PINK1 and Parkin in mitochondrial quality control. Antioxid. Redox Signal. 2011;14:1929-1938.
Narendra et al. PINK1 is selectively stabilized on impaired mitochondria to activate Parkin. PLoS Biol. 2010;8:e1000298.
Novak et al. Nix is a selective autophagy receptor for mitochondrial clearance. EMBO Rep. 2010;11:45-51.
Pankiv et al. p62/SQSTM1 binds directly to Atg8/LC3 to facilitate degradation of ubiquitinated protein aggregates by autophagy. J. Biol. Chem. 2007;282:24131-24145.
Rupprecht et al (2010 Nat Rev Drug Discov. Dec. 2010;9(12):971-88."Translocator protein (18 kDa) (TSPO) as a therapeutic target for neurological and psychiatric disorders".
Soengas. Mitophagy or how to control the Jekyll and Hyde embedded in mitochondrial metabolism: implications for melanoma progression and drug resistance. Pigment Cell Melanoma Res. 2012;25:721-731.
Stępkowski and Kruszewski. Molecular cross-talk between the NRF2/KEAP1 signaling pathway, autophagy, and apoptosis. Free Radic. Biol. Med. 2011;50:1186-1195.
Sureshbabu and Bhandari 2013 Front Physiol 4: 384.
Tufekci et al. 2011. The Nrf2/ARE Pathway: A Promising Target to Counteract Mitochondrial Dysfunction in Parkinson's Disease. Parkinson's Disease. 2011:314082.
Valente et al. Hereditary early-onset Parkinson's disease caused by mutations in PINK1. Science. 2004;304:1158-1160.
Wallace. Mitochondria and cancer. Nat. Rev. Cancer. 2012;12:685-698.
Wohlgemuth et al 2014 J Mol Cell Cardiol 71: 62-70.
Zhu et al. Antioxidants and phase 2 enzymes in macrophages: regulation by Nrf2 signaling and protection against oxidative and electrophilic stress. Exp. Biol. Med. (Maywood) 2008;233:463-474.
Chelli et al., "Platelet 18 kDa Translocator Protein Density is Reduced in Depressed Patients with Adult Separation Anxiety," *Eur. Neuropsychopharmacol*, Abstract, 2008, 18: 249-254.

\* cited by examiner

A

Sulforaphane, 1

PMI, 2

B

A

C

A

B

METHODS OF IDENTIFYING AGENTS HAVING NEUROPROTECTIVE OR ANTI-OXIDANT ACTIVITY FOR REGULATING MITOCHONDRIAL FUNCTION

This application is a U.S. National Stage Application of International Application No. PCT/GB2016/052169, filed Jul. 18, 2016, which was published in English on Jan. 26, 2017, as International Publication No. WO 2017/013416 A1. International Application No. PCT/GB2016/052169 claims priority to British Application No. 1512609.7, filed Jul. 17, 2015.

The present invention relates to the field of modulation of mitochondrial structure and function.

Dysregulation of the destruction of aberrant mitochondria (mitochondrial autophagy, or mitophagy), is implicated in the development and/or progression of a number of diseases such as diabetic nephropathy (Higgins and Coughlan 2014 Br J Pharmacol 171:1917-42); cardiac disease (Wohlgemuth et al 2014 J Mol Cell Cardiol 71: 62-70); cancer (Wallace et al 2012 Nat Rev Cancer 12: 685-698; Soengas 2012 Pigment Cell Melanoma Res 25: 712-731); lung diseases including neonatal lung disease, COPD, lung cancer, asthma and cystic fibrosis (Sureshbabu and Bhandari 2013 Front Physiol 4: 384); and in particular neurodegenerative diseases such as Parkinson's disease, Alzheimer's disease, multiple sclerosis, amyotrophic lateral sclerosis, and Huntington disease (Kamat et al 2014 Cell Biochemistry and Biophysics 70: 707-719; de Castro et al 2010 Epert Rev Mol Med 12:e12; Karbowski et al 2012 Acta Neuropathol 123: 157-171.

The restoration of mitophagy to normal levels or the stimulation of mitophagy to enhanced levels therefore presents an attractive target for the treatment of a wide range of diseases. Although recognized as a fundamental process, selective pharmacologic modulators of mitophagy are almost non-existent and its interplay with the antioxidant response elements (AREs) are little explored (1).

Mitophagy (Kim et al., 2007) is the process by which damaged or dysfunctional mitochondria are selectively engulfed by autophagosomes and delivered to lysosomes to be degraded and recycled by the cell. The most well-recognized mechanism governing the recruitment of autophagosomes to mitochondria is that driven by the PINK1/Parkin pathway (Narendra and Youle, 2011). The PTEN-induced putative kinase 1 (PINK1) accumulates on the outer membrane of dysfunctional mitochondria where it triggers the recruitment of the E3 ubiquitin ligase Parkin (Jin et al., 2010, Narendra et al., 2010, Valente et al., 2004; also known as PARK-2). Once localized to mitochondria, Parkin ubiquitinates several OMM proteins that are consequently targeted by P62/SQSTM1 (Geisler et al., 2010). P62 recognizes ubiquitinated substrates and acts as an adaptor molecule through direct interaction with autophagosome-associated LC3 driving the recruitment of autophagosomal membranes to the mitochondria (Pankiv et al., 2007). Several alternative Parkin-independent mechanisms are also suggested to play a part in mitophagy. Damaged mitochondria can increase FUNDC1 and Nix expression, which may in turn recruit autophagosomes to mitochondria by direct interaction with LC3 (Liu et al., 2012, Novak et al., 2010). Upon mitochondrial depolarization, the ubiquitin ligase Smurf1 also targets mitochondria to induce mitophagy and, recently, the roles of other ubiquitin ligases in mitophagy have been described (Ding and Yin, 2012, Fu et al., 2013, Lokireddy et al., 2012).

The protein P62 is considered to be key as it brings together the mitochondria and the autophagosome. Strategies to enhance the expression or stability of P62 are therefore considered to be beneficial.

The regulation of P62 expression is partly controlled by the transcription factor Nrf2 (nuclear factor erythroid 2-related factor 2), due to the presence of an antioxidant response element (ARE) in its promoter region (Ishii et al., 2000, Jain et al., 2010). Thus, compounds that induce Nrf2 activity have the potential to enhance P62 expression and are potential therapeutics.

Under normal circumstances the redox sensitive ubiquitination facilitator Keap1 (Kelch-like ECH-associated protein 1), binds to Nrf2, resulting in the ubiquitination and degradation of Nrf2, and therefore inhibition of mitophagy (Cheng et al., 2011, Hayes et al., 2010, Kensler et al., 2007). Under oxidative or electrophilic stress, the ubiquitination of Nrf2 is disrupted, resulting in an increase in Nrf2 levels.

A number of electrophilic natural products, including the isothiocyanate compound, sulforaphane and related compound 1, upregulate Nrf2 by covalently modifying cysteine residues in the intervening region of Keap1.

This results in increased concentrations of Nrf2 and in the expression of a range of ARE-dependent gene products involved in phase II metabolism (e.g., glutathione synthesis and conjugation enzymes, NQO1, heme oxygenase-1, etc.) (Hayes et al., 2010, Hong et al., 2010, Zhu et al., 2008) and redox control (e.g., thioredoxin, thioredoxin reductase), in addition to P62 (Jain et al., 2010, Lau et al., 2010, Stępkowski and Kruszewski, 2011). Sulforaphane shows activity in a number of preclinical models of disease prevention, including protection against exposure to oxidizing agents and carcinogens (Kensler et al., 2013). However, the isothiocyanate class of compounds, along with other reactive Nrf2 inducing agents, is capable of interacting with a range of other cysteine-containing proteins within the cell, which can make dissecting their biological activity rather difficult and can lead to toxic off-target effects.

Recently, a compound, P62-mediated mitophagy inducer (PMI) (HB229), was identified that lacks a covalent binding motif and upregulates P62 via stabilization of Nrf2 and promotes mitophagy (East et al 2014 Chemistry and Biology 21: 1585-1596). The compound appears to bypass the upstream steps of the mitophagic cascade, acts independently from the collapse of the $\Delta\Psi_m$, and does not mediate any apparent toxic effects on cells at the concentrations used in the assays.

Gatliff et al (2014) *Autophagy*. 2014;10(12):2279-96."TSPO interacts with VDAC1 and triggers a ROS-mediated inhibition of mitochondrial quality control" reports that TSPO inhibits mitochondrial autophagy downstream of the PINK1-PARK2 pathway, preventing essential ubiquitination of proteins. This document does not suggest that compounds may be assessed by looking at effects on TSPO levels.

The ability to identify further, non-toxic compounds with a similar mode of action, both for use as a therapeutic agent but also as a molecular tool to further dissect mitophagy and the role it plays in both normal fundamental processes and disease pathology, is addressed by the present invention.

Present Invention

We have surprisingly found that the non-toxic Keap-1 inhibitor PMI reduces expression of TSPO, an 18 kDa translocator protein (TSPO) which accumulates on the Outer Mitochondrial Membrane (OMM) and limits cell mitophagy (mitochondrial autophagy) by operating a Reactive Oxygen Species (ROS)-mediated inhibition of the PARK2 dependent ubiquitination. Notably, in sharp contrast to PMI, Sulforaphane (Sulf), a covalent type of Keap-1 inhibitor, is instead unable to induce mitochondrial autophagy despite the evident upregulation of P62/SQSTM1 as the translocation to the mitochondria of P62/SQSTM1 is severely hindered. Additionally, Sulf treatment results in inhibition of the E3 ubiquitin ligase PARK2 mediated ubiquitination without affecting TSPO level. All of this leads to impaired cell mitophagy, which is therefore negatively affected by Sulf.

The present invention highlights that atypical Nrf2-inducers (acting as non-covalent Protein-Protein Interaction Inhibitors) able to modulate cell mitophagy result in a deregulation of TSPO. This implies that both the individual and co-assessment of TSPO reduction and mitophagy activation can identify other compounds acting via the same mechanism of PMI and screen for potential therapeutics and molecular tools.

Upregulation of TSPO (18 kDa Translocator protein; see, for example Rupprecht et al (2010 Nat Rev Drug Discov. 2010 Dec.;9(12):971-88."Translocator protein (18 kDa) (TSPO) as a therapeutic target for neurological and psychiatric disorders"; Feng et al (2014) J Nucl Med. 2014 Dec;55(12):1966-72. doi: 10.2967/jnumed.114.143727. Epub 2014 Nov. 13. In vivo quantification of cerebral translocator protein binding in humans using 6-chloro-2-(4'-123I-iodophenyl)-3-(N,N-diethyl)-imidazo[1,2-a]pyridine-3-acetamide SPECT; Gene ID: 706) has been reported as indicative of tissue inflammation. Pathological conditions (including ageing) that involve inflammation may present overexpressed TSPO. However, we consider that our findings indicate that TSPO overexpression is a primary pro-pathological mechanism associated with the deregulation of mitochondrial quality control via autophagy (termed mitophagy), which highlights a pathogenic mechanism and leads to provision of methods for evaluating and selecting potentially useful substances or treatments.

DETAILED DESCRIPTION OF THE INVENTION

A first aspect of the invention provides a method for assessing whether a test substance or treatment is potentially neuroprotective or anti-oxidant, the method comprising the steps of
  exposing a cell to the test substance or treatment
  assessing the TSPO level in the cell,
  wherein a substance or treatment is considered to be potentially anti-oxidant or neuroprotective if the TSPO level is decreased.

The method may comprise the step of assessing the level of mitophagy as well as the TSPO level in the cell, in which case a substance or treatment is considered to be anti-oxidant or neuroprotective if the level or induction of mitophagy is increased and the TSPO level is decreased.

A second aspect of the invention provides a method for assessing whether a test substance or treatment is potentially able to promote mitophagy, the method comprising the steps of
  exposing a cell to the test substance or treatment
  assessing the TSPO level in the cell, wherein a substance or treatment is considered to be potentially able to promote mitophagy if the TSPO level is decreased.

A third aspect of the invention provides a method for assessing whether a test substance or treatment is potentially useful in the treatment of a disease or condition characterised by aberrant mitochondrial function or aberrant mitophagy, the method comprising the steps of
  exposing a cell to the test substance or treatment
  assessing the TSPO level in the cell,
  wherein a substance or treatment is considered to be potentially useful in the treatment of a disease or condition characterised by aberrant mitochondrial function or aberrant mitophagy if the TSPO level is decreased.

A fourth aspect of the invention provides a method for aiding in determining whether a test substance or treatment leads to non-covalent modification of Keap-1 activity, the method comprising the steps of
  exposing a cell to the test substance or treatment
  assessing the level of mitophagy and/or TSPO level in the cell,
  wherein a substance or treatment is considered to lead to non-covalent modification of Keap-1 activity if the level or induction of mitophagy is increased and/or the TSPO level is decreased.

It is considered that TSPO level may be used to score the efficiency of mitophagy-activating drugs and therefore the potential efficacy of the non-covalent Keap1 inhibitors, potential anti-oxidant and neuroprotective molecules.

It is preferred that the test substance is not a nucleic acid encoding TSPO or a functionally active fragment thereof; or a nucleic acid complementary to a nucleic acid encoding TSPO. For example it is preferred that the test substance is not a cDNA sequence encoding TSPO or an siRNA molecule directed at TSPO.

Downregulation of TSPO is considered indicative of mitophagy activation. The onset of mitophagy is considered to discriminate between covalent and non-covalent Keap-1 inhibitors—therefore the onset of mitophagy or reduction in TSPO level (or assessment of both together) can be used to select potentially anti-oxidant and/or neuroprotective drugs.

Typically for any of the above methods of the invention, the test cell expresses or comprises E3 ubiquitin ligase PARK2 (PARK2 parkin RBR E3 ubiquitin protein ligase Gene ID: 5071). It is considered that most wild-type cells express or comprise E3 ubiquitin ligase PARK2. It is considered that the only cell type so far known to be without PARK 2 is HeLa. It is preferred that the test cell is not a HeLa cell, which is known not to have PARK2. It is preferred that the test cell is not a knockout or knockdown cell or other cell in which PARK2 is known to be missing or reduced, for example through inhibition of knockdown or knockout modification, as well be well known to those skilled in the art.

It is preferred that the test cell is not a TSPO knockout or knockdown cell or other cell in which TSPO is known to be missing or reduced, for example through inhibition or knockdown or knockout modifications. It is considered that TSPO is present in all cells.

The test cell may typically be a human cell but may be any other mammalian cell, for example; for example may be a primate or rodent cell, for example a monkey, rat or mouse cell.

Typically for any of the above methods of the invention, the TPSO level may, for example, be compared with the level before exposure of the cell to the test substance or treatment, or with previously measured reference values, for example, or both, as will be well known to those skilled in the art.

As will be well known to those skilled in the art, the effect of the test substance may be expressed as an IC50 eg the amount of test substance expected to inhibit the measure in question by 50%, typically based on a dose response curve.

Typically the TSPO level that may be assessed is the level of TSPO mRNA, optionally using an RT-PCR method. Suitable methods will be well known to those skilled in the art.

Alternatively or in addition, the TSPO level assessed may be the level of TSPO protein, optionally using an immuno-quantitation method. As an example, a Western blot-based method may be used. Examples of Western blotting of TSPO are described in the Examples. Further suitable methods will be apparent to the skilled person. For example, please see Gatliff et al (2014) 10; 2279-2296.

As a further alternative or in addition, the TSPO level that is assessed may be the level of TSPO activity, optionally by assessing mitochondrial cholesterol accumulation. For example, please see Gatliff et al (2014) 10; 2279-2296.

Analysis of TSPO ligand binding degree in vivo or in vitro (intact cells) may also be useful in assessing TSPO level changes. TSPO ligands and ways of using them to assess TSPO levels are well known (because TSPO has been considered and used as a marker of microglial activation) and include, for example, ligands described in WO 2012/168697 or Owen et al (2010) Cereb Blood Flow Metab 1608-1618 or Owen et al (2012) Cereb Blood Flow Metab 32(1) 1-5. As noted in these documents it may be necessary to determine what allele of TSPO is present as different alleles may have different binding affinities for different ligands. TSPO ligand binding may be assessed using TSPO imaging techniques, as well known to those skilled in the art, which typically makes use of fluorescent-labelled TSPO ligands or TSPO ligands labelled appropriately for PET (positron emission tomography): see, for example, examples referred to in WO 2012/168697 or Owen et al (2010) Cereb Blood Flow Metab 1608-1618 or Owen et al (2012) Cereb Blood Flow Metab 32(1) 1-5.

Thus, in one illustrative example, the invention provides a method for assessing whether a test substance or treatment is potentially neuroprotective or anti-oxidant, the method comprising the steps of exposing a cell to the test substance or treatment and assessing the TSPO level in the cell by adding to the cell one or more fluorescent labelled TSPO ligands. As will be apparent to those skilled in the art, fluorescence may typically be assessed by imaging, but may alternatively be assessed by other techniques, such as fluorescence activated cell sorting (FACS).

The assessment of mitophagy (when performed) may typically comprise one or more of assessment of the level of expression of a mtDNA encoded protein or proteins, optionally assessment of the level of expression of MTCO-1 imaging of mitochondria, optionally imaging of number and/or morphology of mitochondria and/or assessment of mitochondrial membrane potential ($\Delta\Psi_m$).

Thus, for example, a reduced level of expression of an mtDNA encoded protein or proteins, optionally of MTCO-1, indicates an increased level of or increased activation of mitophagy. Nonetheless, the tailoring of mitochondrial network by autophagy can alternatively be imaged by using the analysis of LC3 recruitment on mitochondria via means of immunocytochemistry or mitochondrial fractionation.

Examples are provided in the Examples. Assessment of mitophagy is also described in East et al (2014) Chemistry & Biology 21, 1585-1596, for example.

Particularly in relation to the third aspect of the invention, the aberrant mitophagy may typically be reduced response mitophagy.

The disease or condition characterised by aberrant mitochondrial function or aberrant mitophagy may be, for example, diabetic nephropathy (Higgins and Coughlan 2014 Br J Pharmacol 171:1917-42); cardiac disease (Wohlgemuth et al 2014 J Mol Cell Cardiol 71: 62-70); cancer (Wallace et al 2012 Nat Rev Cancer 12: 685-698; Soengas 2012 Pigment Cell Melanoma Res 25: 712-731); lung diseases including neonatal lung disease, COPD, lung cancer, asthma and cystic fibrosis (Sureshbabu and Bhandari 2013 Front Physiol 4: 384); neurodegenerative diseases such as Parkinson's disease, Parkinsonism, Alzheimer's disease, multiple sclerosis, amyotrophic lateral sclerosis, and Huntington disease (Kamat et al 2014 Cell Biochemistry and Biophysics 70: 707-719; de Castro et al 2010 Expert Rev Mol Med 12:e12; Karbowski et al 2012 Acta Neuropathol 123: 157-171. The disease or condition may be characterised by increased TSPO levels, for example increased TSPO protein, binding activity, activity or mRNA level.

The cell may typically be a cell in tissue culture, but may also be a cell in organ culture. Thus the method may be performed in vitro or ex vivo.

Examples of suitable cell types may include a mouse embryonic fibroblast cell; a SH-SY5Y cell, a SH-SY5Y cell treated with MPP+, a Hepa1c1c7 cell.

As noted above, typically the cell may express or comprise PARK2. In some situations it may be desirable to conduct an assay with a cell that does not have PARK2, for example as a control test. Thus, for example, a HeLa cell (which is considered not to have a competent PARK2 system) may be used as a control cell, for example as in the Examples.

A method of the invention may also be performed with a cell that is a cell in organ culture, optionally wherein the method comprises assessing the TSPO level in the cell. TSPO Ligand binding or imaging methods (for example as discussed above) may be particularly useful when the cell is in organ culture.

A method of the invention may also be performed wherein the cell is in a test animal, for example a mouse or a monkey. Thus the method may be performed in vivo (for example using imaging techniques, as discussed above, though typically the assay would be performed in vitro or ex vivo. See also, for example, Ciccarelli O et al (2014) Pathogenesis of multiple sclerosis: insights from molecular and metabolic imaging. Lancet Neurol. 2014 Aug.; 13(8):807-22.

It may be appropriate to se the downregulation of TSPO as a measure of how a subject is responding to treatment, for example with a PMI-like drug, either in using a known compound or treatment, or in assessing a test compound or treatment. TSPO Ligand binding or imaging methods may be used, for example, for example using PET with appropriately labelled TSPO ligands.

As will be well known to those skilled in the art, further investigations and tests will be necessary in identifying, developing and/or refining a substance (which may be a composition comprising one or more chemical species) or treatment, for example in establishing safety, bioavailability and efficacy parameters. Thus, the methods of the present invention may be used alongside other steps in investigating and developing a substance or treatment.

The listing or discussion of an apparently prior-published document in this specification should not necessarily be taken as an acknowledgement that the document is part of the state of the art or is common general knowledge.

Preferences and options for a given aspect, feature or parameter of the invention should, unless the context indicates otherwise, be regarded as having been disclosed in combination with any and all preferences and options for all other aspects, features and parameters of the invention.

The invention will now be described in more detail by reference to the following, non-limiting, Figures and Examples.

FIGURE LEGENDS

FIG. 1—PMI and sulforaphane regulate mitochondrial protein levels in alternative fashion (A) Structures of compounds 1 (sulforaphane) and 2 (PMI).

(B) The Proposed Working Model for PMI.

(C) Western blot to compare β-subunit levels in MEF cells following 24 h treatment with DMSO vehicle control, 1 μM sulforaphane or 10 μM PMI. [β-actin is shown as a loading control.

(D) Graph shows MTCO-1:β-actin ratio band density analysis, n=3.

All values are mean±SEM, $*p<0.05$, $p<0.01$, $*p<0.001$.

FIG. 2—The PMI-induced mitophagy is blocked by Sulphoraphane (A) Western blot to demonstrate p62 and MTCO-1 levels in MEF cells treated with either DMSO vehicle control, or PMI (10 μM), or sulforaphane (1 μM), or co-administration (10 μM PMI & 1 μM sulforaphane). B-actin is shown as a loading control.

(B and C) Graphs show P62:β-actin (B) and MTCO-1:β-actin (C) ratio band density analysis, n=3.

(D) Representative images of LC3 localization in MEF cells treated with DMSO vehicle control, or 1 μM sulforaphane and/or 10 μM PMI for 24 hr. Scale bar represents 10 μm. A magnification of the merge images is shown in areas demarcated by the white box.

All values are mean±SEM, $*p<0.05$, $p<0.01$, $*p<0.001$.

FIG. 3—The PMI-induced mitochondrial protein ubiquitination and P62 translocation are inhibited by Sulforaphane (A) Representative images of P62 localization in MEF cells treated with DMSO vehicle control, or 1 μM sulforaphane and/or 10 μM PMI for 24 hr. Scale bar represents 10 μm. A magnification of the merge images is shown in areas demarcated by the white box. Scale bar represents 10 μm.

(B) Western blot of mitochondrial fractions, highlighting mitochondrial ubiquitination in control or sulforaphane and/or PMI-treated MEF cells. B-subunit is shown as a loading control; n=2.

FIG. 4—Sulforaphane halts basal PARK2 translocation (A and B) Western blot highlighting different levels of PARK2 in the mitochondrial fraction of MEFs treated with sulforaphane and/or PMI (A) and quantified in (B); n=3.

(C and D) Western blot highlighting no increase in PARK2 in the cytosolic fraction of MEFs treated with sulforaphane and/or PMI (C) and quantified in (D); n=2.

(E) Representative images of PARK2 localization in MEF cells treated with DMSO vehicle control or 1 μM sulforaphane and/or 10 μM PMI for 24 hr, before and after treatment with FCCP (20 μM) for 4 hr. Scale bar represents 10 μm. A magnification of the merge images is shown in areas demarcated by the white box.

FIG. 5—Sulforaphane and PMI equally promote mitophagy in PARK2-deficient cells without modifying TSPO expression in these cells (A) Western blot to demonstrate p62, MTCO-1 and TSPO levels in MEF cells treated with either DMSO vehicle control, or sulforaphane (1 μM), and/or PMI (10 μM) for 24 h. B-actin is shown as a loading control. (B) Western blot to demonstrate p62 and MTCO-1 levels in HeLa cells treated with either DMSO vehicle control, or sulforaphane (1 μM), and/or PMI (10 μM) for 8 h. B-actin is shown as a loading control. (C) Graph shows MTCO-1:β-actin ratio band density analysis, n=3. (D) Graph shows P62:β-actin ratio band density analysis, n=3.

All values are mean±SEM, $*p<0.05$, $p<0.01$, $*p<0.001$.

FIG. 6—PMI down-regulates TSPO expression level which associates with the induction of mitophagy (A) Western blot to compare β-subunit, MTCO-1 and TSPO levels in MEFs treated with either DMSO vehicle control, or sulforaphane (1 μM), or PMI (10 μM) either with or without co-administration of UO126 (10 μM) for 24 h. B-actin is shown as a loading control.

(B) Graph show MTCO-1:β-actin (B), β-subunit:β-actin (C), TSPO:β-actin ratio band density analysis, n=3.

(D) RT-PCR analysis for estimation of TSPO mRNA levels in MEFs following treatment with DMSO, PMI (10 μM) and/or sulforaphane (1 μM). Values are presented as arbitrary units normalized to 18s RNA levels for each sample, n≥3.

All values are mean±SEM, $*p<0.05$, $p<0.01$, $*p<0.001$.

FIG. 7—Schematic Model summarises the mechanism of action for the atypical Nrf-2 activators acting via a non-covalent mechanisms The data reported in this manuscript demonstrate that:
1) PMI is a non-covalent inhibitor of Keap1.
2) Sulforaphane halts the Nrf2-induced mitophagy by suppressing mitochondrial ubiquitination
3) Sulforaphane does not affect the expression of TSPO neither in PARK2 null cells (HeLa) nor in MEF cells, while PMI decreases TSPO levels in MEFs, but not in the cells in which PARK2 is not expressed such as HeLa cells.

This work highlights the downregulation of TSPO expression as a valuable and simple method to assess the efficacy of PPI inhibitors and define these as mitophagy activators in PARK2 competent cells compared to covalent Nrf2.

FIG. 8 The PD Toxins MPP$^+$ and 6-HOD upregulate TSPO to sustain oxidative stress accumulation a. Representative immunofluorescence of TSPO in SHY-5Y Cells. Panels b and c: Immunoblot analysis of TSPO expression pattern and ATPB5 in SHY-5Y Cells treated with MPP$^+$ and 6-OHD.

Finally, panel d depicts traces and histogram-values of Reactive Oxygen Species dynamics in neurons transiently deregulated for TSPO before and after MPP+ addition thus suggesting that sporadic inducers of PD directly affect TSPO expression level and this as a pathogenic mechanism leading to impairment of cell mitophagy occurring via accumulation of the oxidative stress.

EXAMPLES

Example 1

Sulforaphane Increases the Amount of Mitochondrial Proteins, Whilst PMI Decreases the Amount of Mitochondrial Proteins in PARK2 Competent Cells In an effort to expand our understanding of the relationship between Nrf2 and mitophagy, we decided to build on our recent findings (East et al., 2014) and explore the effects of different mechanisms of Keap1 inhibition on this process.

PMI, a non-electrophilic inducer of Nrf2, and sulforaphane, an isothiocyanate that halts the Keap1-mediated destruction of Nrf2 via covalent modifications, were used as chemical probes in this study.

To confirm the mode of action of PMI, a series of biochemical experiments were conducted with human Keap1 Kelch protein. According to the results, PMI is able to disrupt the protein-protein interaction between Keap1 and Nrf2 in a dose-dependent manner and is able to do so, without causing a degradation of the Keap1 Kelch protein. These experiments validate the non-covalent interaction of PMI with Keap1, which reduces significantly the scope for off-target effects compared to electrophilic Nrf2 activators, such as sulforaphane.

Figure 1:
FIG. 1(A) shows the structure of sulforaphane and PMI, whilst
FIG. 1(B) shows the proposed working model for PMI, in which Nrf-2 is released from Keap1, localised in the nucleus to effect transcription of P62 (amongst others), resulting in the colocalisation of mitochondria and the autophagosome, and the destruction of the mitochondria.
FIG. 1(c) shows previously reported work (East et al., 2014), indicating that whilst sulforaphane treatment results in an increase in mitochondrial proteins (as assayed by the detection of mitochondrial cytochrome oxidase 1 beta subunit (MTCO-1), PMI treatment does not, implying that despite the up-regulation of Nrf2 and its downstream gene product P62, mitophagy is not induced by sulforaphane.
Figure 1:
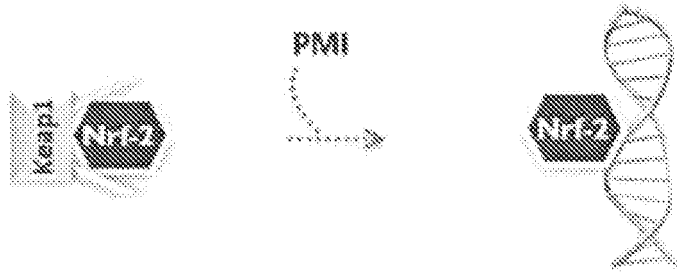
Figure 1:
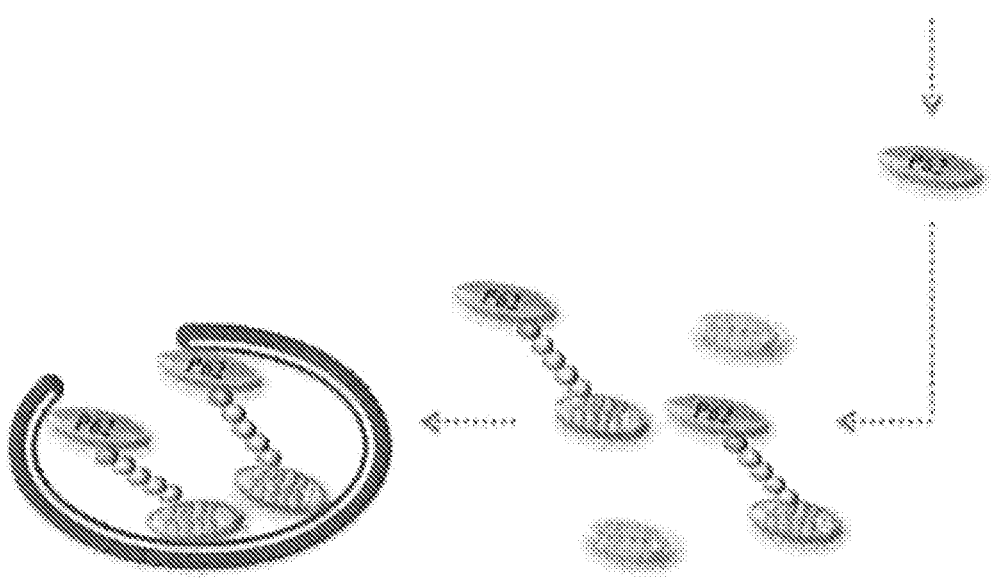
Figure 1:
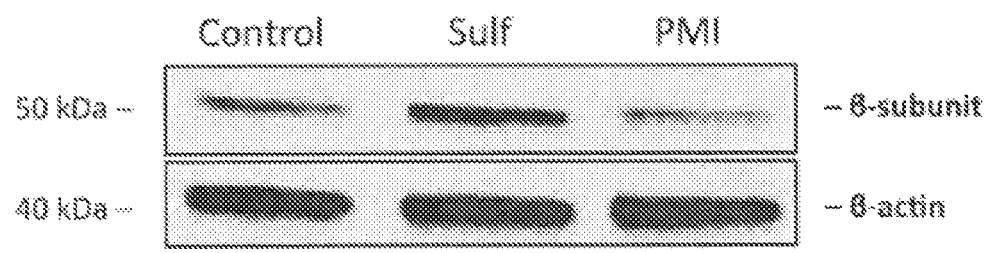
Figure 2:
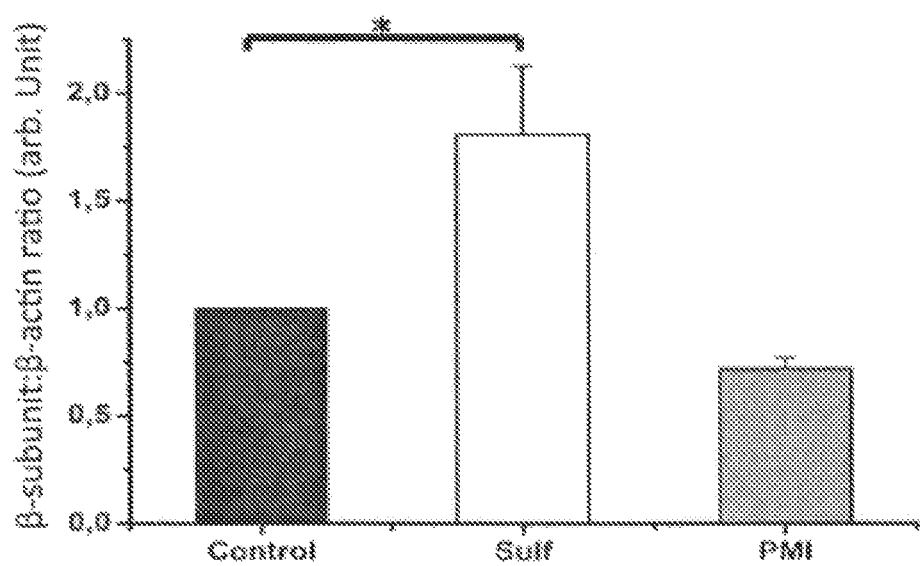
Figures 1, 2:
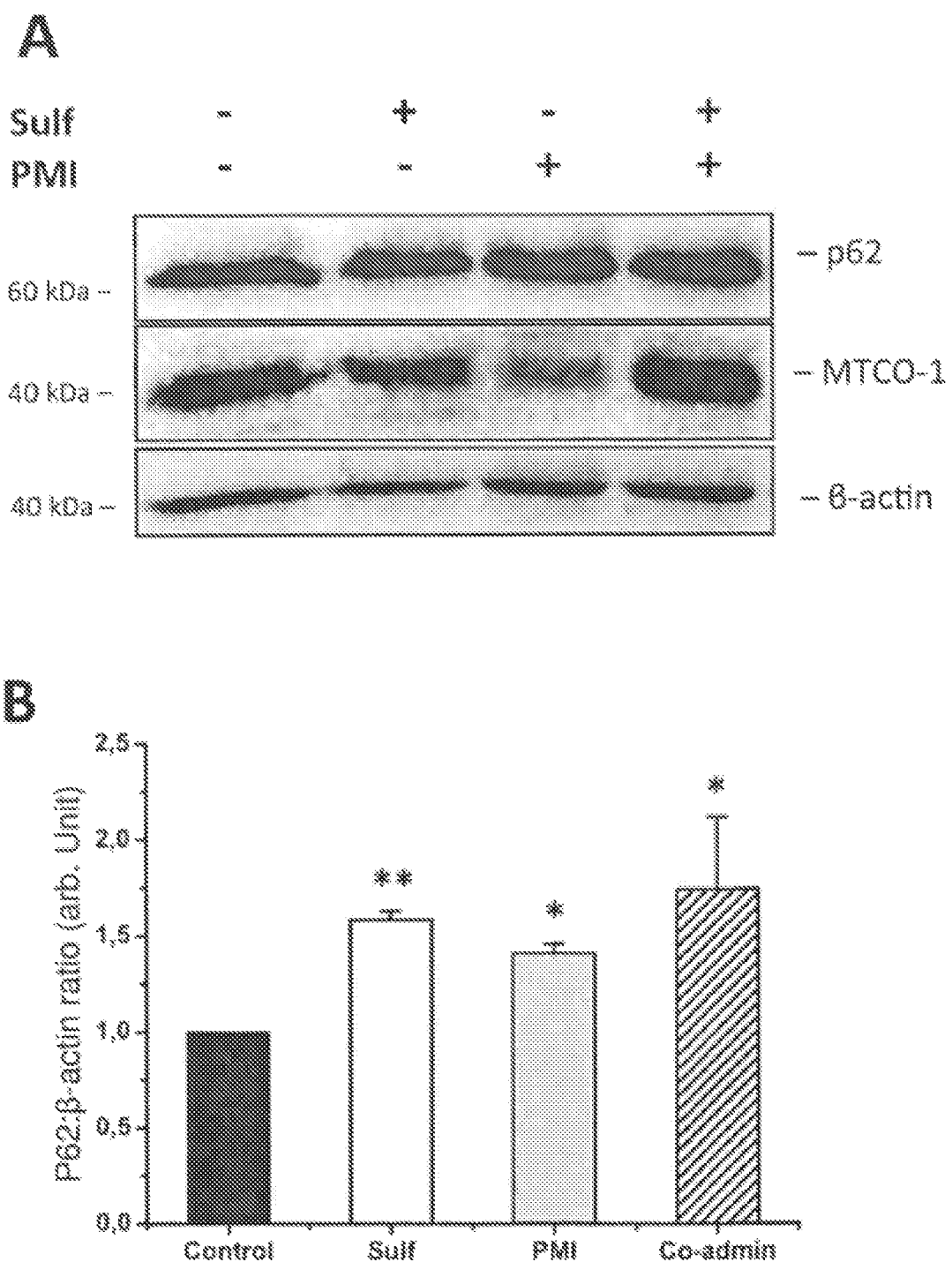
Figure 2:
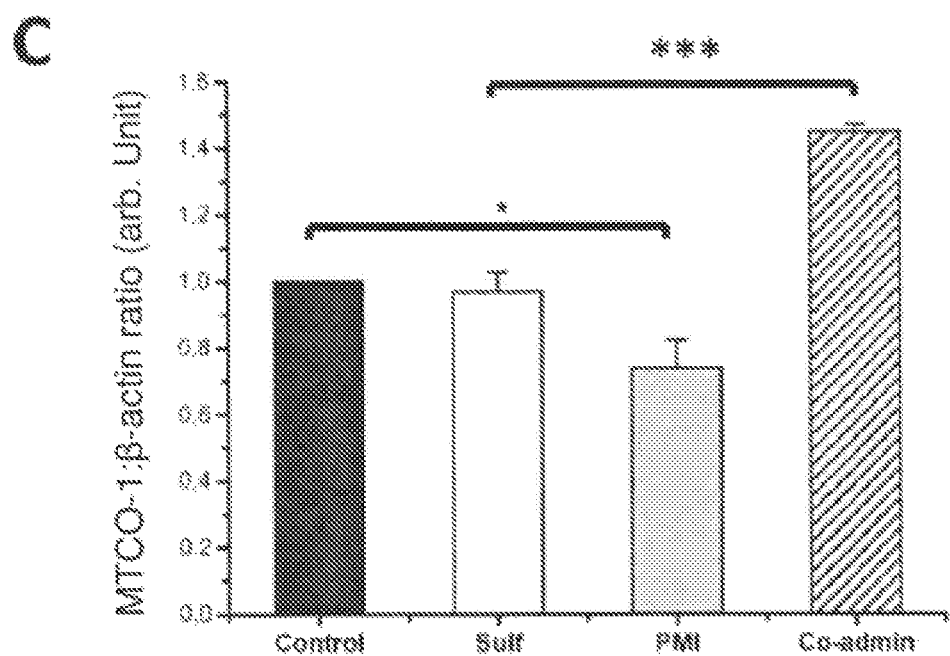

FIG. 2A-C indicate that Sulforaphane inhibits the Nrf2-induced reduction of mitochondrial protein levels.

To investigate the effects of sulforaphane in mitophagy, we examined the colocalisation of mitochondria and LC-3 in MEF cells using high-resolution confocal imaging (FIG. 2D). As expected, in PMI-treated cells the mitochondrial LC3 colocalisation was significantly increased compared to untreated cells. However, in cells treated with sulforaphane no induction of mitophagy was observed. Surprisingly, the mitochondrial LC3 colocalisation attributed to PMI was abolished by addition of sulforaphane.

Figures 2, 3:
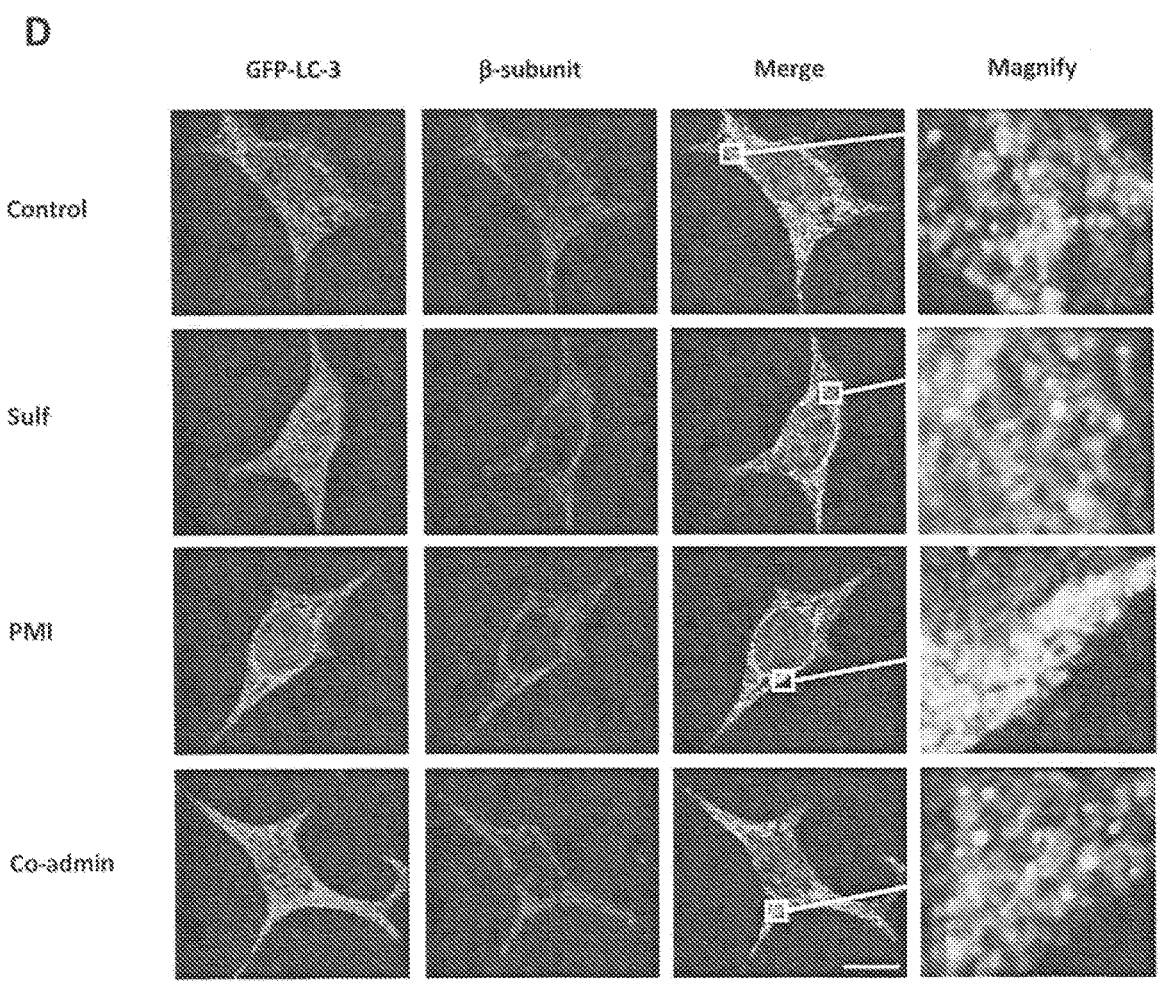
Figures 1, 3:
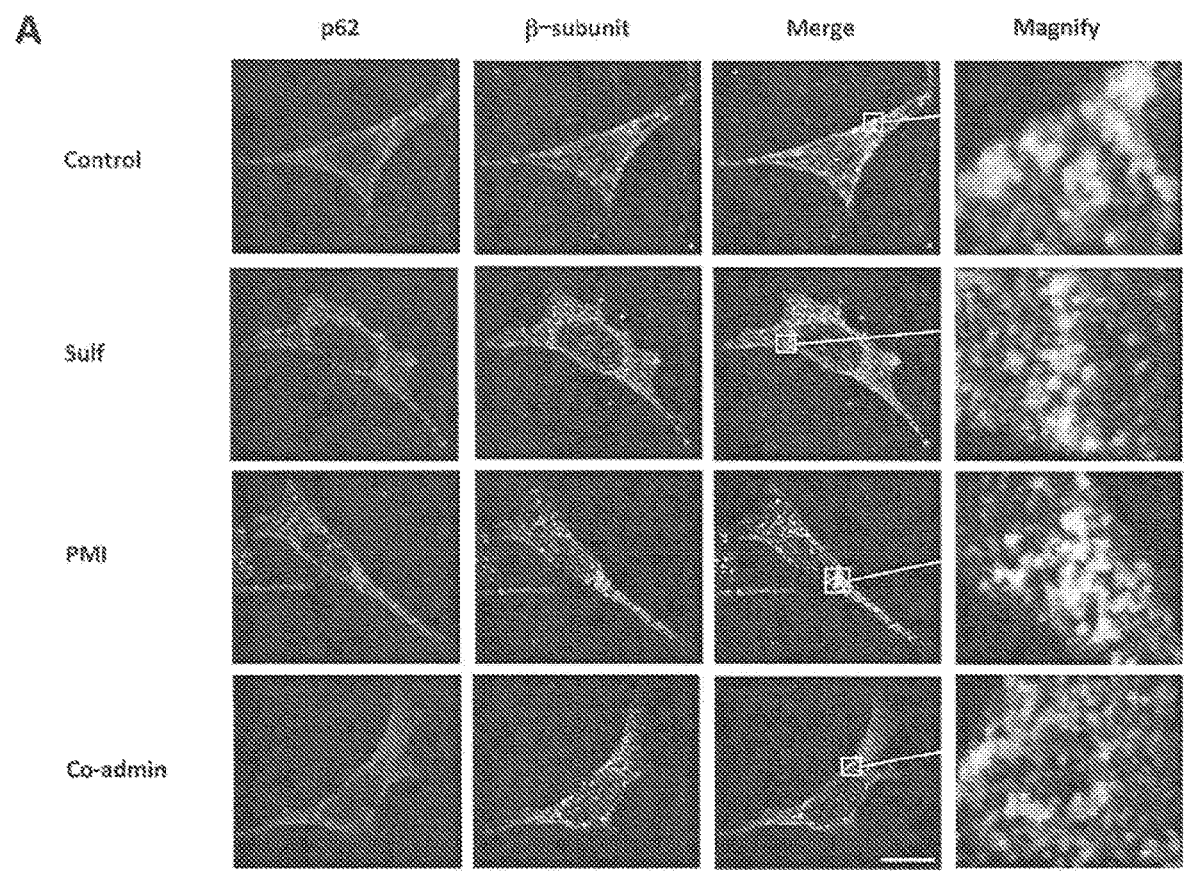
Figures 2, 3:
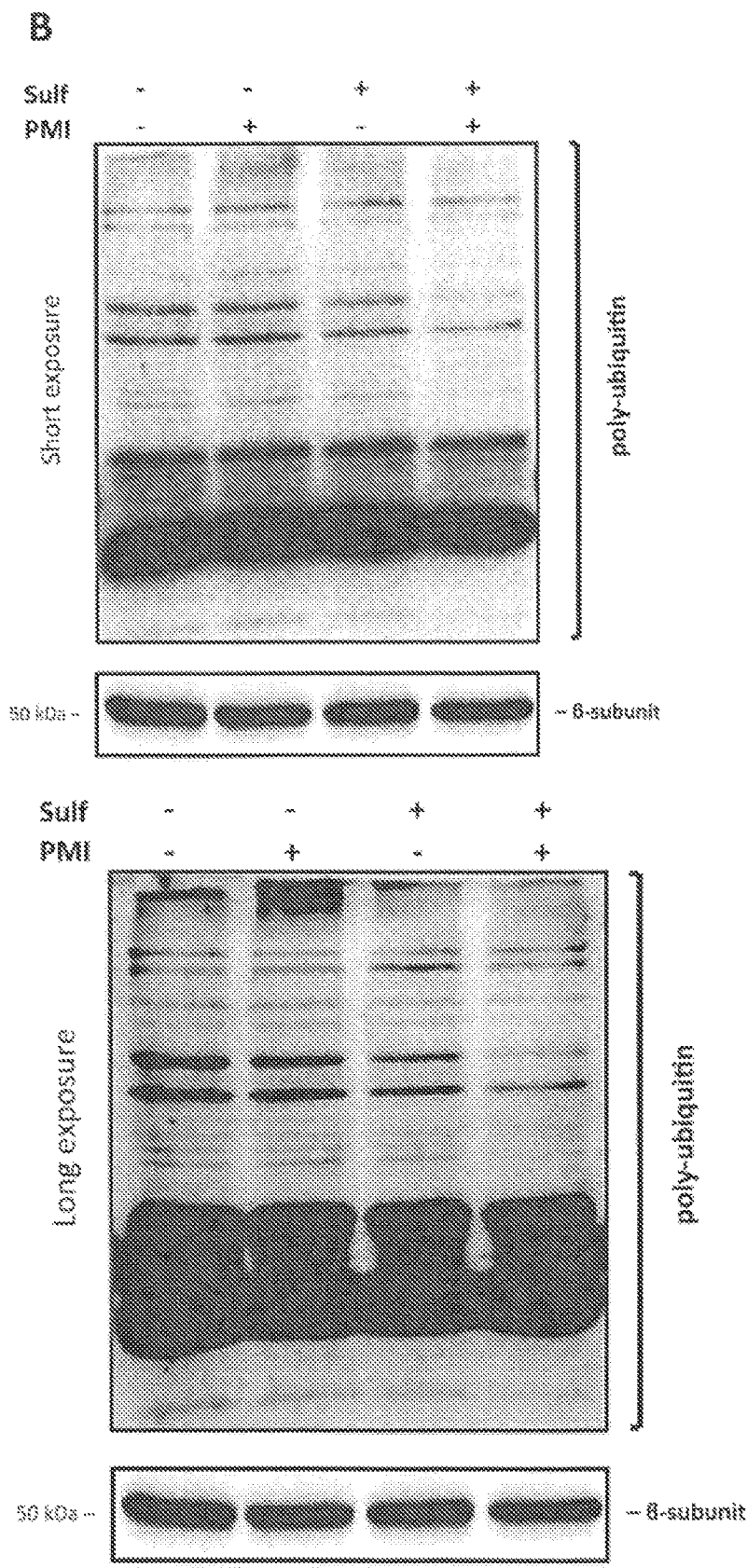

The levels and localisation of p62 in MEF cells were then examined by immunoblotting (FIG. 3A). Treatment with sulforaphane for 24 h resulted in increased levels of p62 in the cytosol compared to control. However, its translocation to mitochondria was impaired and significantly reduced compared to basal conditions. This prompted us to investigate the ubiquitination status of mitochondrial proteins, which is a required stimulus for the translocation of p62. An increased ubiquitination was observed in mitochondrial fractions of MEF cells treated with PMI for 24 h compared to the vehicle control, while co-administration of sulforaphane abolished the effect attributed to PMI (FIG. 3B).

Figure 4:
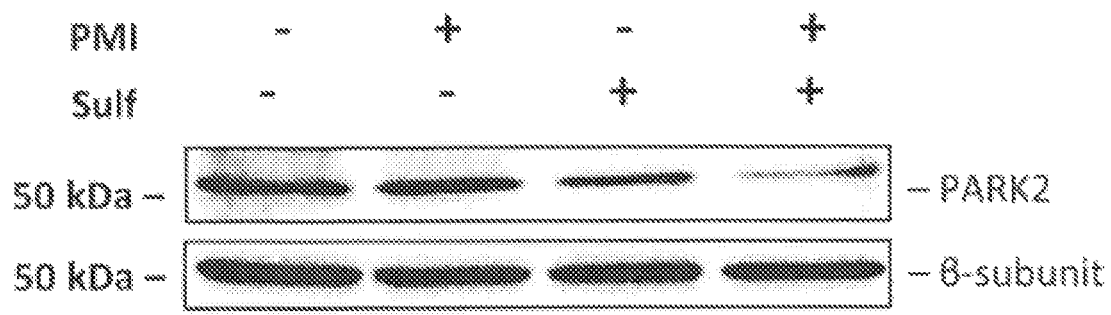
Figure 1:
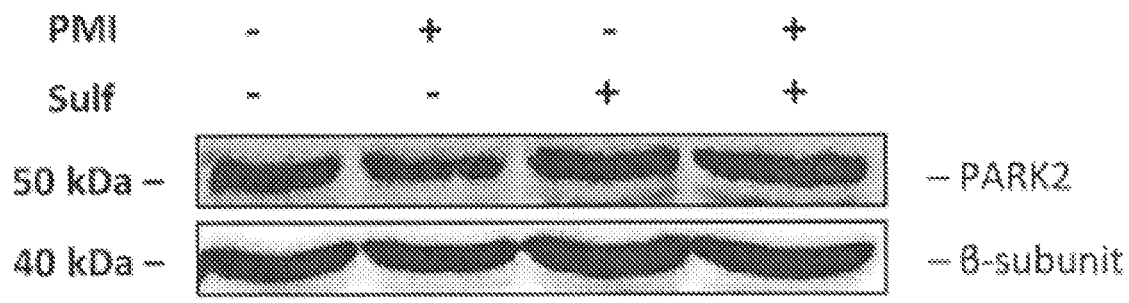
Figures 2, 4:
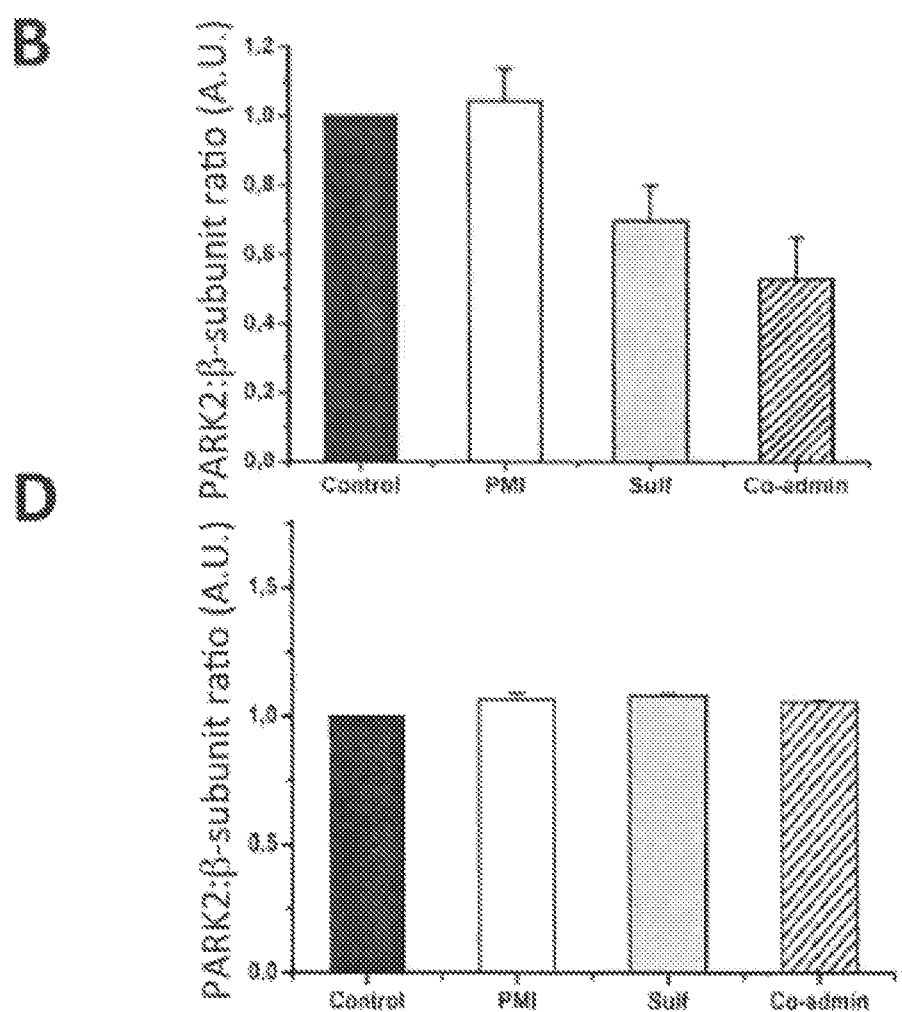
Figures 3, 4:
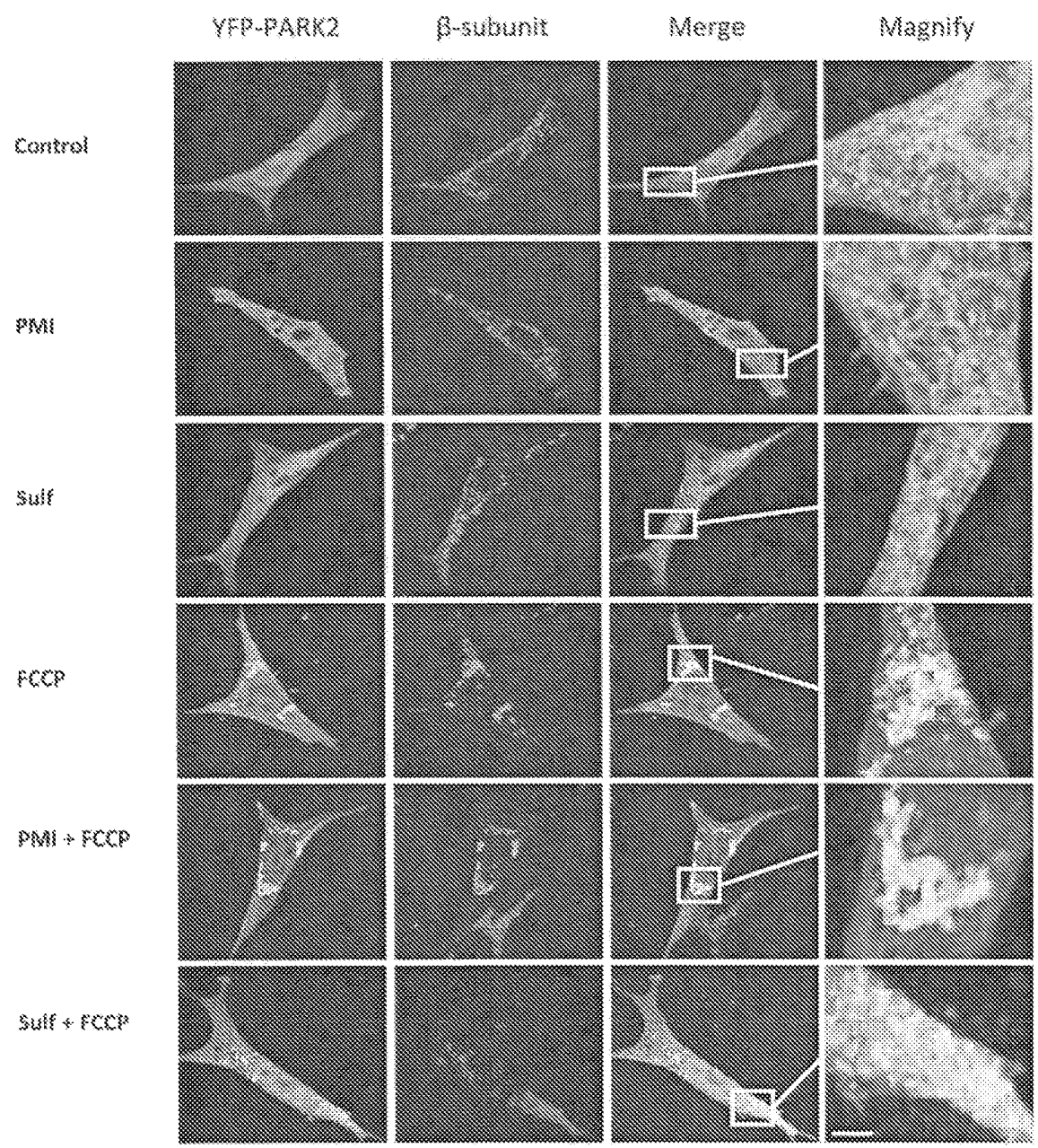

We then investigated if the inhibitory effect of sulforaphane on mitochondrial protein ubiquitination is a result of its interference either directly or indirectly with the activity of the E3 ligase Parkin (FIGS. 3B and C). We therefore examined the ability of PARK2 to translocate to mitochondria either under basal conditions or after Carbonyl cyanide-4-(trifluoromethoxy)phenylhydrazone (FCCP an ionophore) treatment. The levels of PARK2 in mitochondrial fractions of MEF cells treated with sulforaphane for 24 h were reduced compared to the vehicle control, while no statistically significant differences were observed in PMI treated cells (FIGS. 4A and B). Addition of PMI did not alter the reduced activity of PARK2, which was attributed to sulforaphane.

We then performed immunocytochemistry experiments to confirm the above results and examine if sulforaphane is able to inhibit the FCCP-induced PARK2 translocation in MEF cells (FIG. 4E). However, no statistically significant differences were observed between the vehicle control and cells treated with PMI and/or sulforaphane when FCCP was used as a stimulus.

Figure 5:
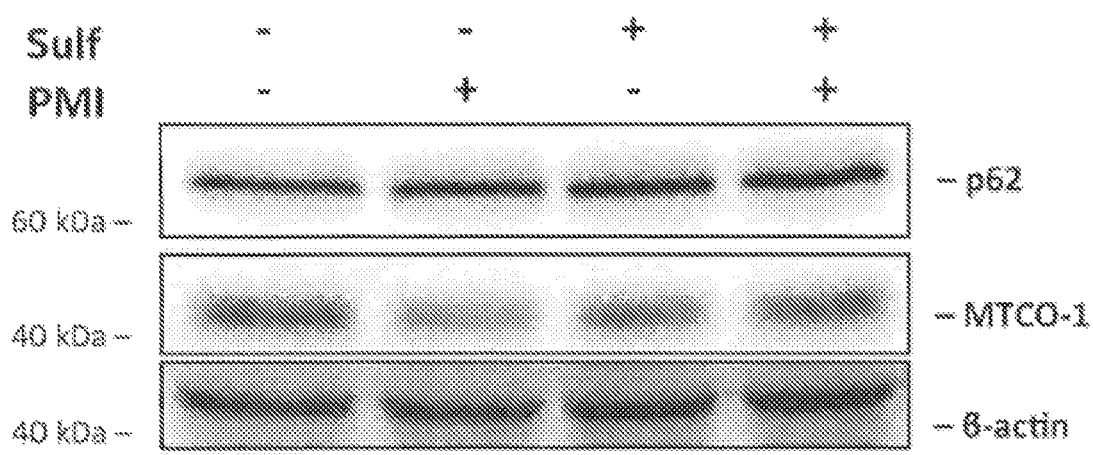
Figure 1:
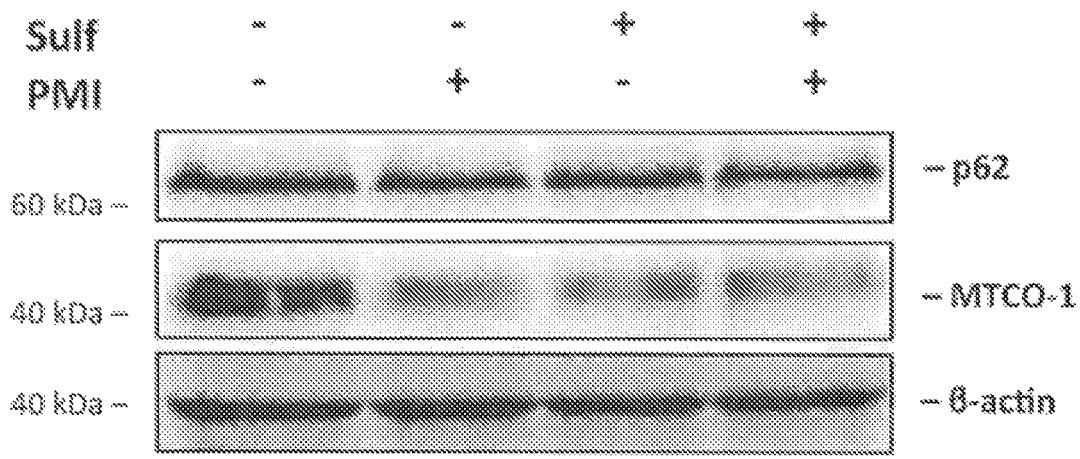
Figure 5:
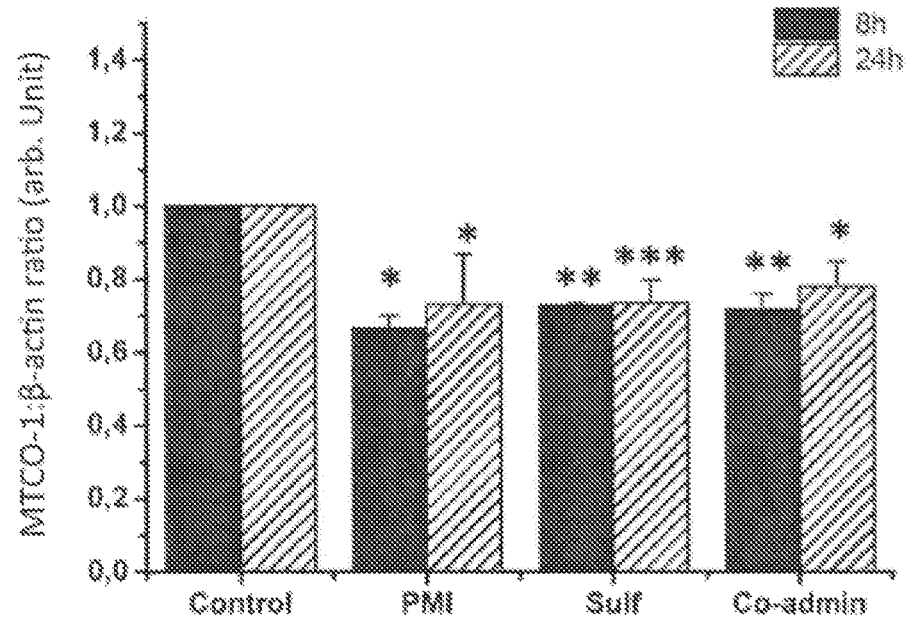
Figure 2:
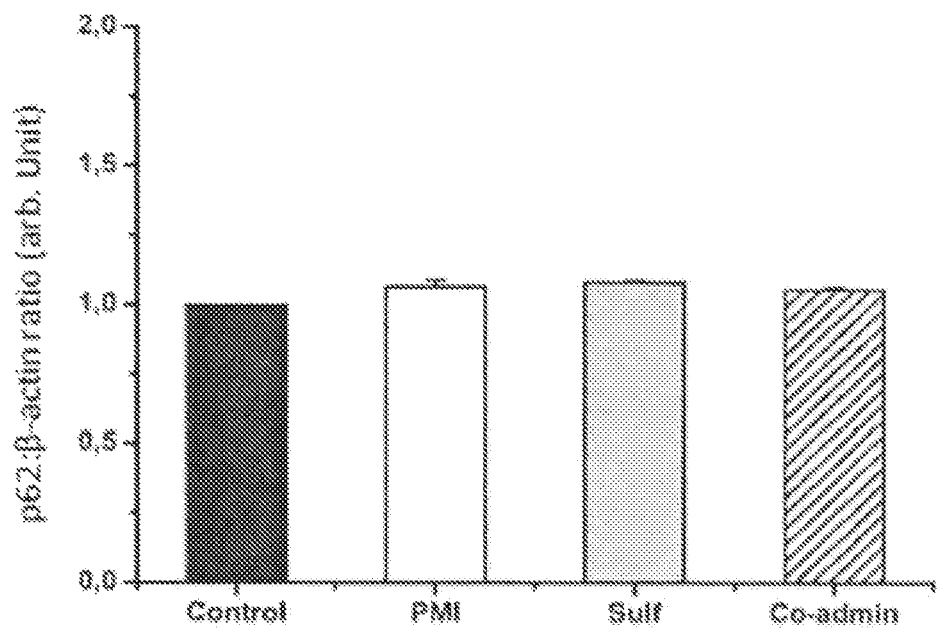

To further validate these results, HeLa cells that have null levels of endogenous PARK2 were co-transfected with mt-RFP and YFP-PARK2 and degree of translocation was examined by live imaging (FIG. 5). In all conditions (DMSO, PMI, sulforaphane), PARK2 translocation was initiated after 30 mins of FCCP treatment regardless of whether the cells were pre- or co-treated. Moreover, almost complete co-localisation of PARK2 in mitochondria was observed after approximately 60 mins of FCCP treatment. This prompted us to further investigate the inhibitory effect of sulforaphane and PMI on mitophagy and examine the levels of key mitochondrial proteins via western blot using. In MEF cells, 24 h treatment of PMI resulted in a reduced mitochondrial network, while no significant differences were observed between sulforaphane-treated and untreated cells. However, co-administration of sulforaphane and PMI resulted in a significant normalization of the mitochondrial protein levels. The same experiment was repeated in HeLa cells (after 7 h and 24 h) in which surprisingly induction of mitophagy was observed under all three conditions at both time points (FIGS. 5A and B).

Figures 1, 6:
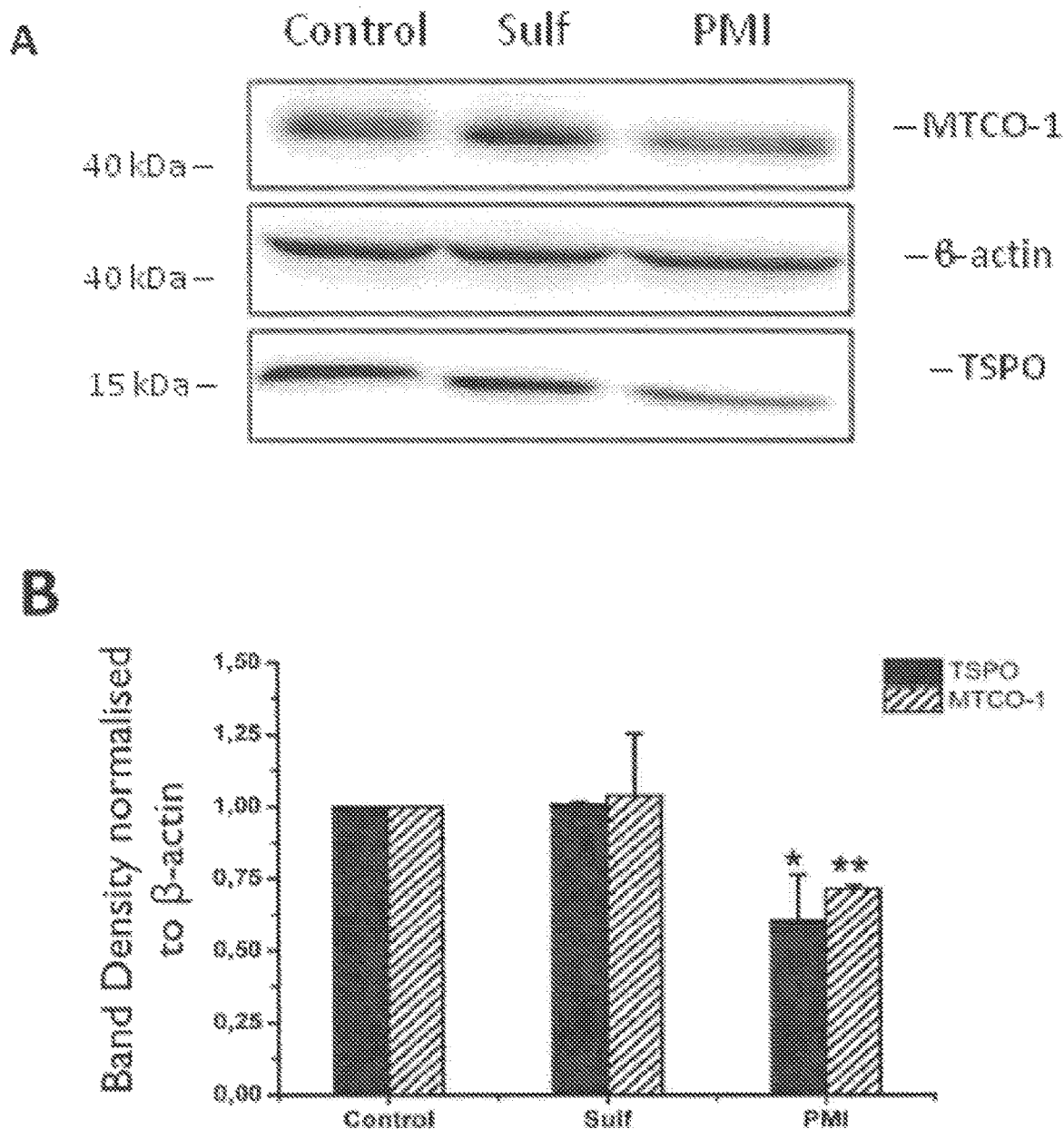
Figure 6:
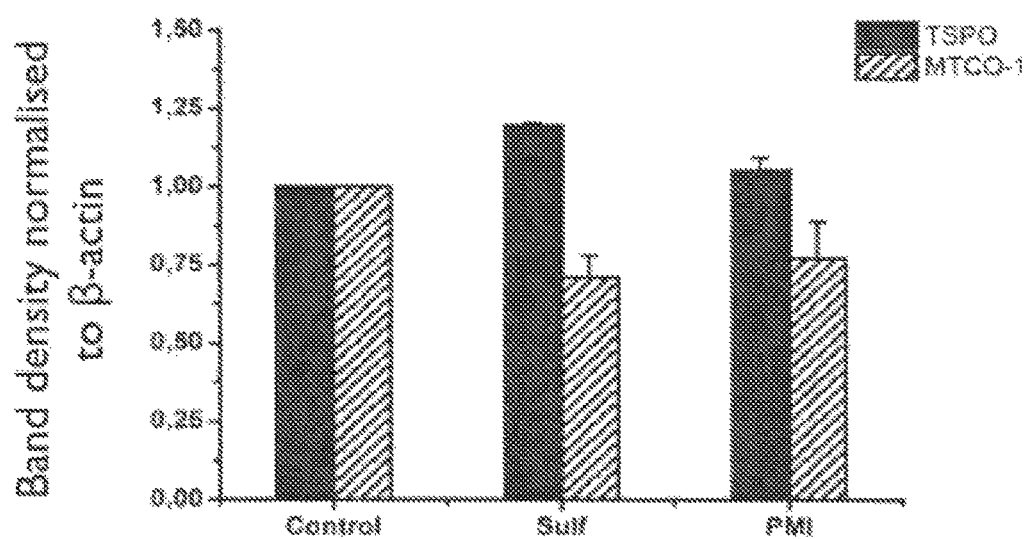
Figure 2:
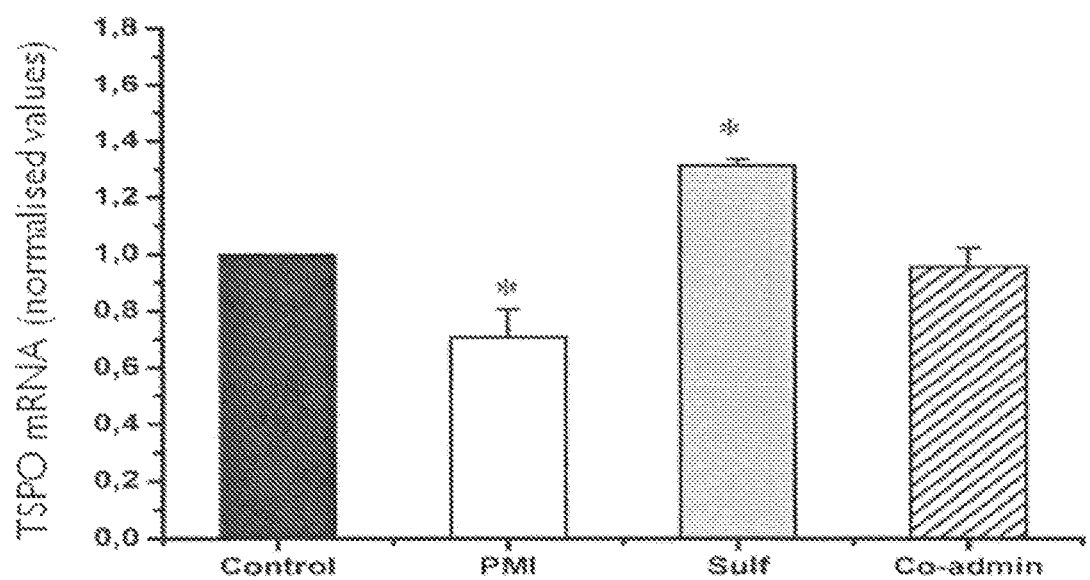
Figure 7:
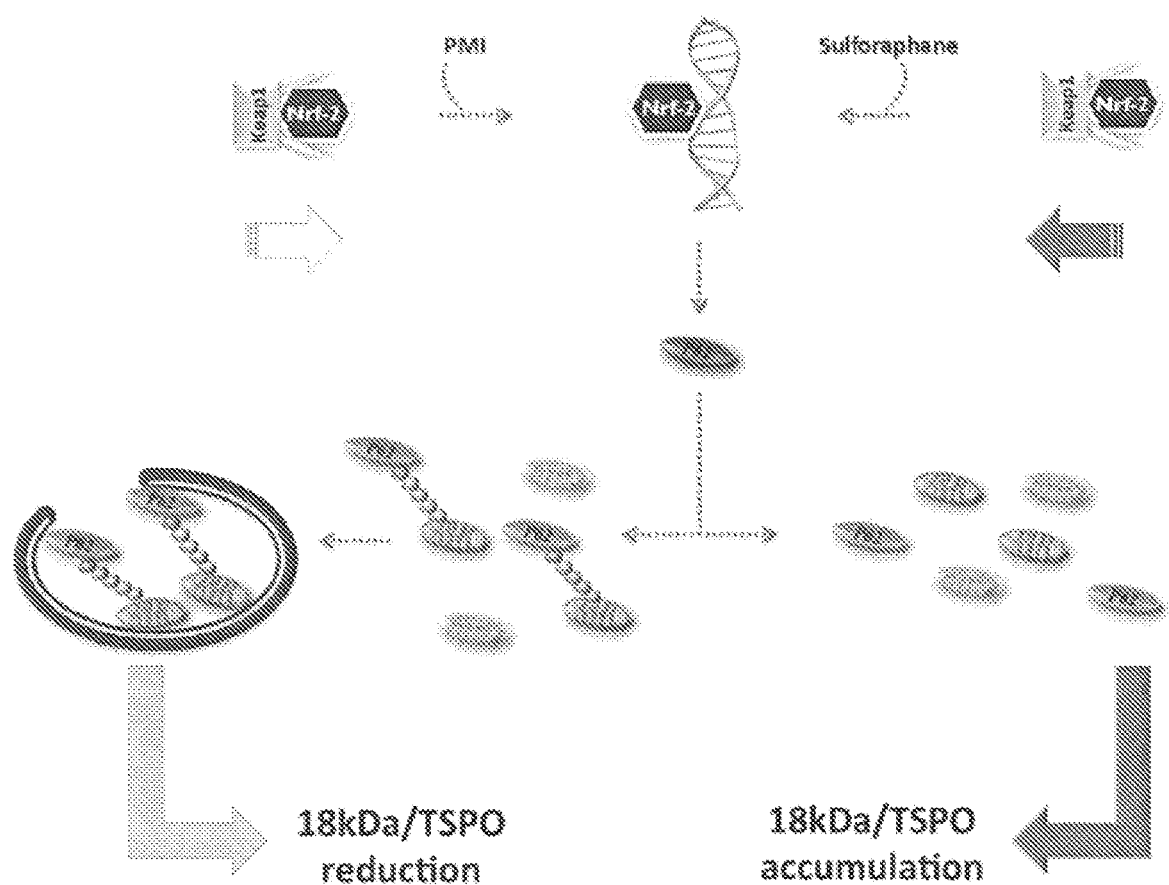
Figures 1, 8:
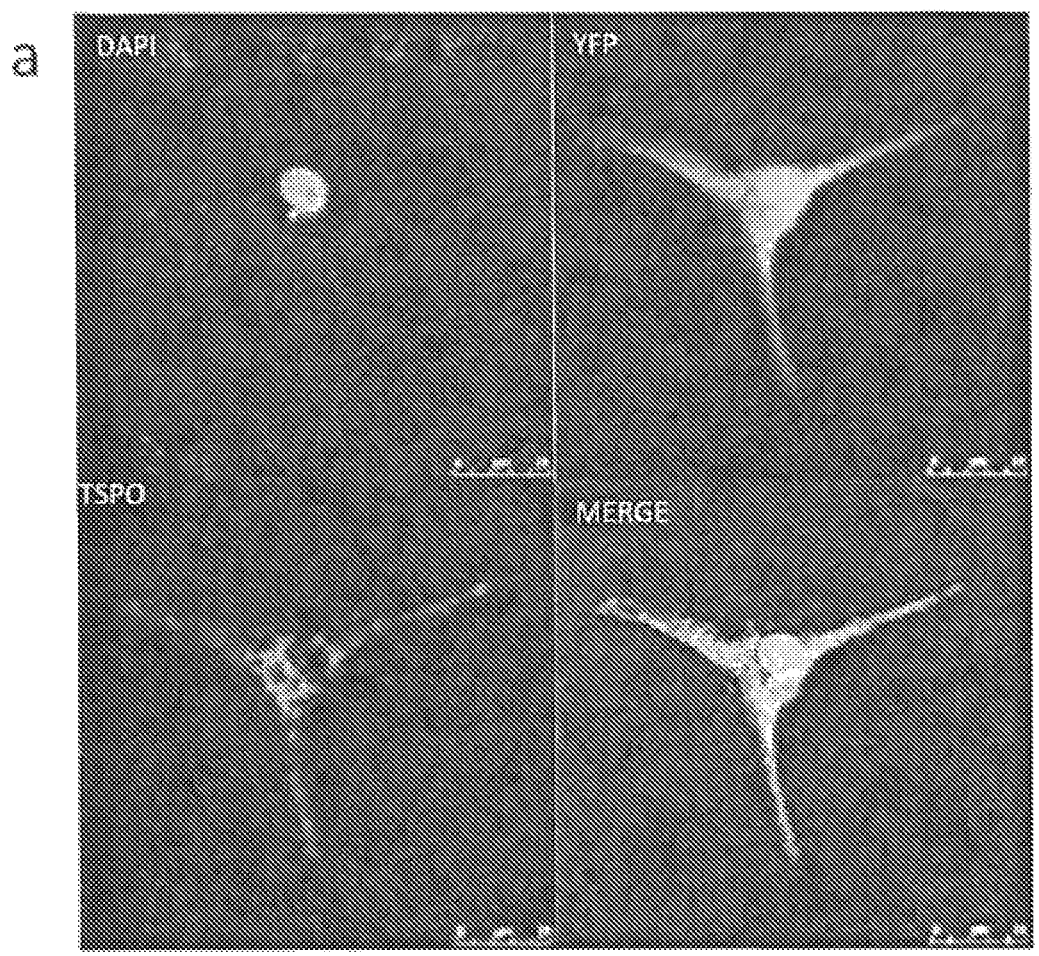
Figures 2, 8:
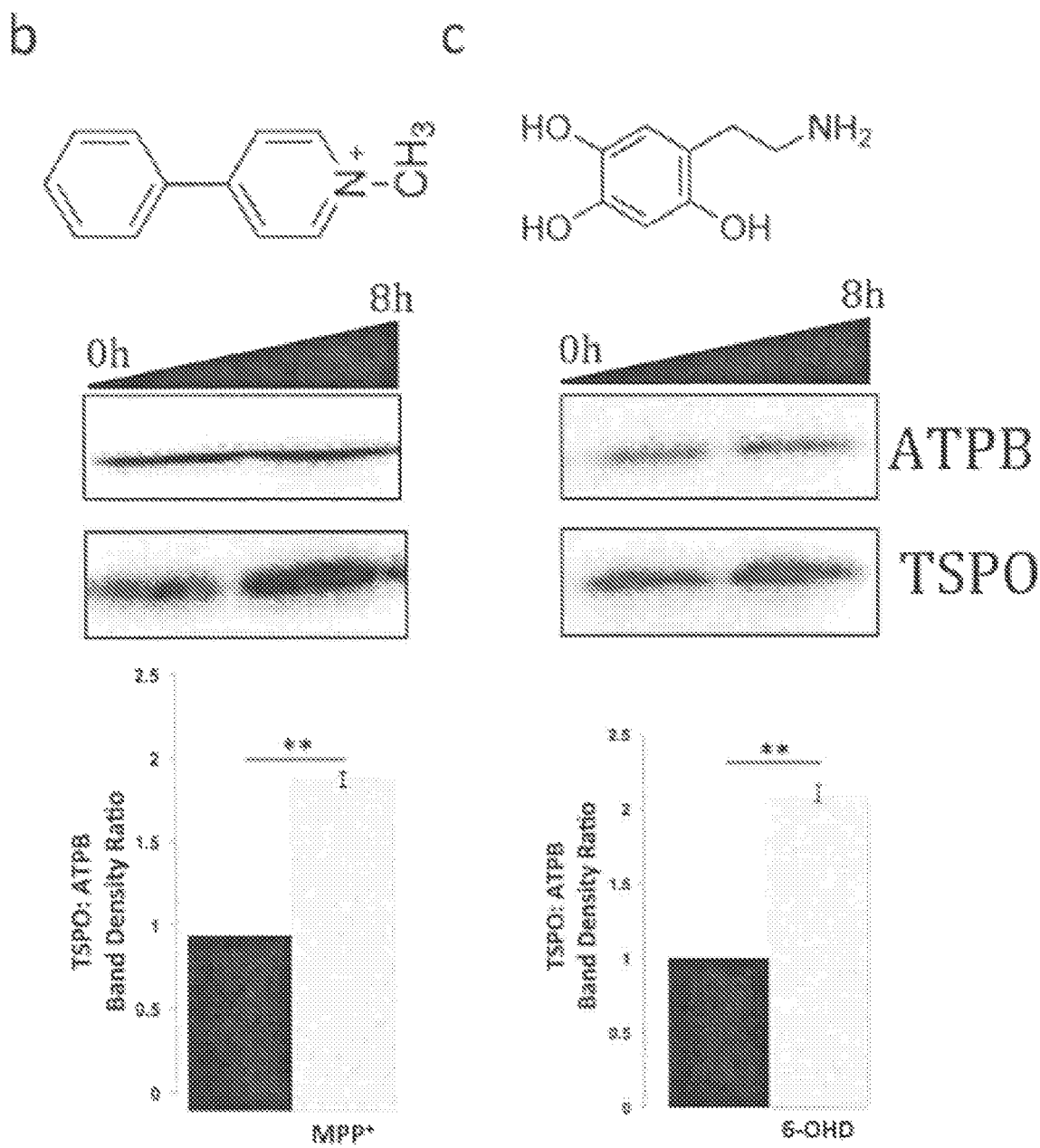
Figures 3, 8:
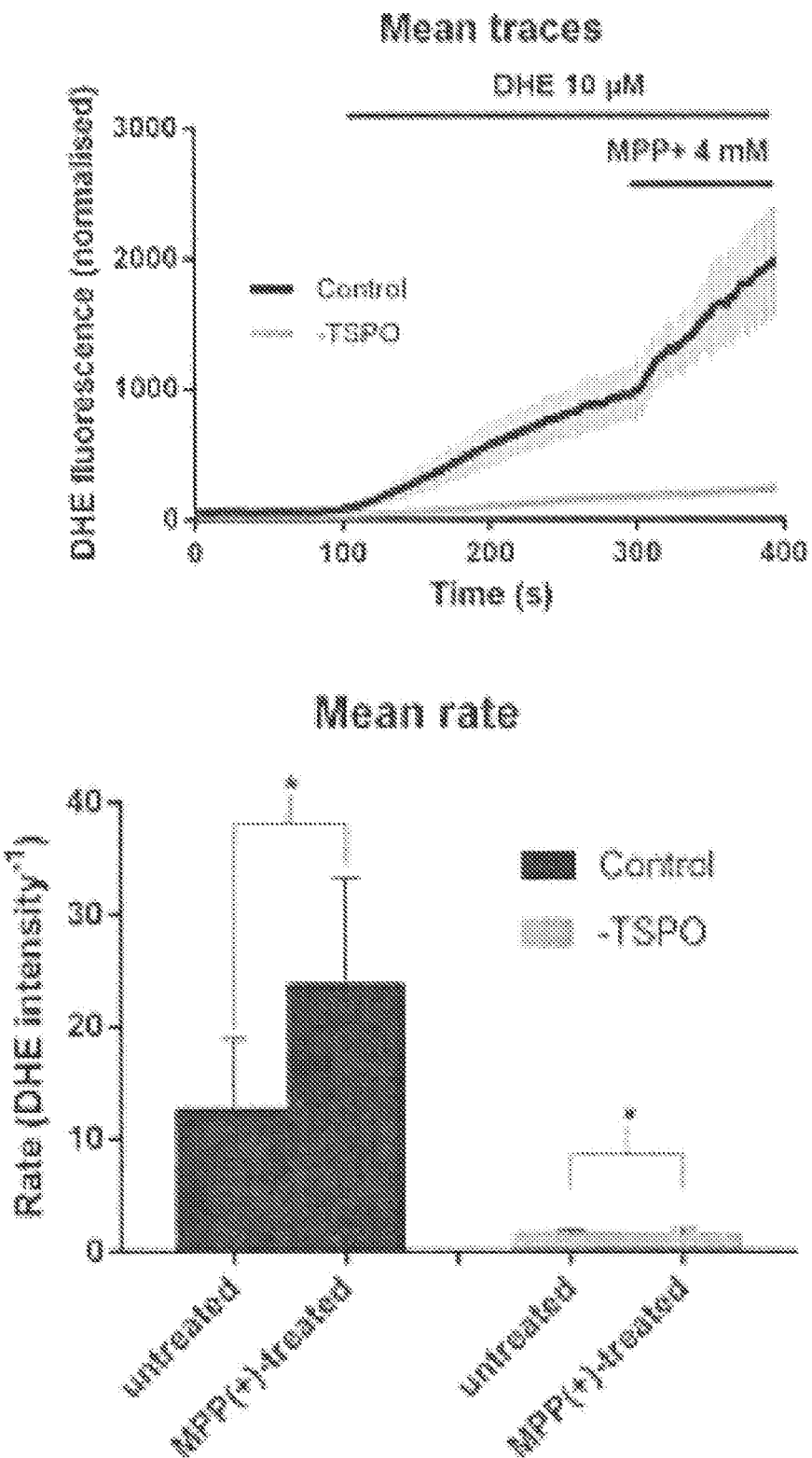

TSPO has been recently described as a modulator of mitophagy (Gatliff et al., 2014). We were therefore interested to examine if PMI and sulforaphane alter its accumulation on Mitochondria as well as its transcription levels FIG. 6E. The levels of TSPO by immunoblotting were therefore tested and revealed that PMI did cause a reduction in the levels of TSPO compared to control and sulforaphane treated cells, in which no significant differences were observed (FIG. 6A) and quantified (FIG. 6B, C). RT-PCR was then performed from samples obtained from MEF cells after 24 h treatments with DMSO or PMI and/or sulforaphane showing the same pattern of result and thus in cells treated with PMI the levels of TSPO mRNA were reduced compared to control, while in sulforaphane treated cells a statistically significant increase was observed (FIG. 6D).

The expression of TSPO is known to be related to the Erk1/2 activity and a recent publication from Hirota et al. (2015) has also proposed a pivotal role of the Erk pathway in alternative mechanisms of mitophagy. It is therefore possible that the effects of PMI on mitophagy are due to an activation of this pathway through induction of some Nrf2-downstream gene products that leads to the down regulation of TSPO expression. Because the expression of this mitophagy limiting factor is insensitive to Sulforaphane treatment, TSPO is proposed here as a read-out for non-covalent Keap-1 inhibitors considered to be efficacious on neuroprotective mechanisms such as mitophagy.

REFERENCES

1. Matic I, Strobbe D, Frison M and Campanella M. Controlled and impaired Mitochondrial Quality in neurons: Molecular Physiology and Prospective Pharmacology. Pharmacological Research in press 2. East D, Fagiani F, Crosby J, Bertrand H, Schaap M, Fowkes A, Wells G, and Campanella M. PMI: a novel, $\Delta\Psi m$ independent, Mitophagy Inducer". Chem Biol. 2014 Nov. 20;21(11):1585-96.

3. Gatliff J, East D, Crosby J, Abeti R Harvey R, Craigen W, Parker P and Campanella M. TSPO interacts with VDAC1 and triggers a ROS-mediated inhibition of mitochondrial quality control. Autophagy 2014 Dec. 2;10(12):2279-96.

Abrahams J. P., Leslie A. G., Lutter R., Walker J. E. Structure at 2.8 A resolution of F1-ATPase from bovine heart mitochondria. Nature. 1994;370:621-628.

Baird L., Dinkova-Kostova A. T. The cytoprotective role of the Keap1-Nrf2 pathway. Arch. Toxicol. 2011;85:241-272.

Capaldi R. A. Structure and function of cytochrome c oxidase. Annu. Rev. Biochem. 1990;59:569-596.

Cheng X., Siow R. C., Mann G. E. Impaired redox signaling and antioxidant gene expression in endothelial cells in diabetes: a role for mitochondria and the nuclear factor-E2-related factor 2-Kelch-like ECH-associated protein 1 defense pathway. Antioxid. Redox Signal. 2011;14:469-487.

Chu C. T. A pivotal role for PINK1 and autophagy in mitochondrial quality control: implications for Parkinson disease. Hum. Mol. Genet. 2010;19(R1):R28-R37.

Chu C. T., Ji J., Dagda R. K., Jiang J. F., Tyurina Y. Y., Kapralov A. A., Tyurin V. A., Yanamala N., Shrivastava I. H., Mohammadyani D. Cardiolipin externalization to the outer mitochondrial membrane acts as an elimination signal for mitophagy in neuronal cells. Nat. Cell Biol. 2013;15:1197-1205.

de Castro I. P., Martins L. M., Tufi R. Mitochondrial quality control and neurological disease: an emerging connection. Expert Rev. Mol. Med. 2010;12:e12.

Denison S. R., Wang F., Becker N. A., Schüle B., Kock N., Phillips L. A., Klein C., Smith D. I. Alterations in the common fragile site gene Parkin in ovarian and other cancers. Oncogene. 2003;22:8370-8378.

Ding W. X., Yin X. M. Mitophagy: mechanisms, pathophysiological roles, and analysis. Biol. Chem. 2012;393:547-564.

Ding W. X., Ni H. M., Li M., Liao Y., Chen X., Stolz D. B., Dorn G. W., 2nd, Yin X. M. Nix is critical to two distinct phases of mitophagy, reactive oxygen species-mediated autophagy induction and Parkin-ubiquitin-p62-mediated mitochondrial priming. J. Biol. Chem. 2010;285:27879-27890.

Fahey J. W., Dinkova-Kostova A. T., Stephenson K. K., Talalay P. The "Prochaska" microtiter plate bioassay for inducers of NQO1. Methods Enzymol. 2004;382:243-258.

Faucher N., Ambroise Y., Cintrat J. C., Doris E., Pillon F., Rousseau B. Highly chemoselective hydrogenolysis of iodoarenes. J. Org. Chem. 2002;67:932-934.

Fu M., St-Pierre P., Shankar J., Wang P. T., Joshi B., Nabi I. R. Regulation of mitophagy by the Gp78 E3 ubiquitin ligase. Mol. Biol. Cell. 2013;24:1153-1162.

Geetha T., Vishwaprakash N., Sycheva M., Babu J. R. Sequestosome 1/p62: across diseases. Biomarkers. 2012;17:99-103.

Geisler S., Holmström K. M., Skujat D., Fiesel F. C., Rothfuss O. C., Kahle P. J., Springer W. PINK1/Parkin-mediated mitophagy is dependent on VDAC1 and p62/SQSTM1. Nat. Cell Biol. 2010;12:119-131.

Hayes J. D., McMahon M., Chowdhry S., Dinkova-Kostova A. T. Cancer chemoprevention mechanisms mediated through the Keap1-Nrf2 pathway. Antioxid. Redox Signal. 2010;13:1713-1748.

Heytler P. G., Prichard W. W. A new class of uncoupling agents—carbonyl cyanide phenylhydrazones. Biochem. Biophys. Res. Commun. 1962;7:272-275.

Hirose S., Yaginuma N., Inada Y. Disruption of charge separation followed by that of the proton gradient in the mitochondrial membrane by CCCP. J. Biochem. 1974;76:213-216.

Holmström K. M., Baird L., Zhang Y., Hargreaves I., Chalasani A., Land J. M., Stanyer L., Yamamoto M., Dinkova-Kostova A. T., Abramov A. Y. Nrf2 impacts cellular bioenergetics by controlling substrate availability for mitochondrial respiration. Biol. Open. 2013;2:761-770.

Hong Y., Yan W., Chen S., Sun C. R., Zhang J. M. The role of Nrf2 signaling in the regulation of antioxidants and detoxifying enzymes after traumatic brain injury in rats and mice. Acta Pharmacol. Sin. 2010;31:1421-1430.

Huang C., Andres A. M., Ratliff E. P., Hernandez G., Lee P., Gottlieb R. A. Preconditioning involves selective mitophagy mediated by Parkin and p62/SQSTM1. PLoS ONE. 2011;6:e20975.

Ishii T., Itoh K., Takahashi S., Sato H., Yanagawa T., Katoh Y., Bannai S., Yamamoto M. Transcription factor Nrf2 coordinately regulates a group of oxidative stress-inducible genes in macrophages. J. Biol. Chem. 2000;275:16023-16029.

Jain A., Lamark T., Sjøttem E., Larsen K. B., Awuh J. A., Øvervatn A., McMahon M., Hayes J. D., Johansen T. p62/SQSTM1 is a target gene for transcription factor NRF2 and creates a positive feedback loop by inducing antioxidant response element-driven gene transcription. J. Biol. Chem. 2010;285:22576-22591.

Jin S. M., Youle R. J. PINK1- and Parkin-mediated mitophagy at a glance. J. Cell Sci. 2012;125:795-799.

Jin S. M., Youle R. J. The accumulation of misfolded proteins in the mitochondrial matrix is sensed by PINK1 to induce PARK2/Parkin-mediated mitophagy of polarized mitochondria. Autophagy. 2013;9:1750-1757.

Jin S. M., Lazarou M., Wang C., Kane L. A., Narendra D. P., Youle R. J. Mitochondrial membrane potential regulates PINK1 import and proteolytic destabilization by PARL. J. Cell Biol. 2010;191:933-942.

Kabeya Y., Mizushima N., Ueno T., Yamamoto A., Kirisako T., Noda T., Kominami E., Ohsumi Y., Yoshimori T. LC3, a mammalian homologue of yeast Apg8p, is localized in autophagosome membranes after processing. EMBO J. 2000;19:5720-5728. [PubMed]

Karbowski M., Neutzner A. Neurodegeneration as a consequence of failed mitochondrial maintenance. Acta Neuropathol. 2012;123:157-171.

Kawajiri S., Saiki S., Sato S., Sato F., Hatano T., Eguchi H., Hattori N. PINK1 is recruited to mitochondria with parkin and associates with LC3 in mitophagy. FEBS Lett. 2010;584:1073-1079.

Kensler T. W., Wakabayashi N., Biswal S. Cell survival responses to environmental stresses via the Keap1-Nrf2-ARE pathway. Annu. Rev. Pharmacol. Toxicol. 2007;47:89-116.

Kensler T. W., Egner P. A., Agyeman A. S., Visvanathan K., Groopman J. D., Chen J. G., Chen T. Y., Fahey J. W., Talalay P. Keap1-nrf2 signaling: a target for cancer prevention by sulforaphane. Top. Curr. Chem. 2013;329:163-177.

Kim I., Rodriguez-Enriquez S., Lemasters J. J. Selective degradation of mitochondria by mitophagy. Arch. Biochem. Biophys. 2007;462:245-253.

Klionsky D. J., Abdalla F. C., Abeliovich H., Abraham R. T., Acevedo-Arozena A., Adeli K., Agholme L., Agnello M., Agostinis P., Aguirre-Ghiso J. A. Guidelines for the use and interpretation of assays for monitoring autophagy. Autophagy. 2012;8:445-544.

Lau A., Wang X. J., Zhao F., Villeneuve N. F., Wu T., Jiang T., Sun Z., White E., Zhang D. D. A noncanonical mechanism of Nrf2 activation by autophagy deficiency: direct interaction between Keap1 and p62. Mol. Cell. Biol. 2010;30:3275-3285.

Liu L., Feng D., Chen G., Chen M., Zheng Q., Song P., Ma Q., Zhu C., Wang R., Qi W. Mitochondrial outer-membrane protein FUNDC1 mediates hypoxia-induced mitophagy in mammalian cells. Nat. Cell Biol. 2012;14:177-185.

Lokireddy S., Wijesoma I. W., Teng S., Bonala S., Gluckman P. D., McFarlane C., Sharma M., Kambadur R. The ubiquitin ligase Mul1 induces mitophagy in skeletal muscle in response to muscle-wasting stimuli. Cell Metab. 2012;16:613-624.

Matsuda N., Sato S., Shiba K., Okatsu K., Saisho K., Gautier C. A., Sou Y. S., Saiki S., Kawajiri S., Sato F. PINK1 stabilized by mitochondrial depolarization recruits Parkin to damaged mitochondria and activates latent Parkin for mitophagy. J. Cell Biol. 2010;189:211-221.

Morelli A., Chiozzi P., Chiesa A., Ferrari D., Sanz J. M., Falzoni S., Pinton P., Rizzuto R., Olson M. F., Di Virgilio F. Extracellular ATP causes ROCK I-dependent bleb formation in P2X7-transfected HEK293 cells. Mol. Biol. Cell. 2003;14:2655-2664.

Murata H., Sakaguchi M., Kataoka K., Huh N. H. SARM1 and TRAF6 bind to and stabilize PINK1 on depolarized mitochondria. Mol. Biol. Cell. 2013;24:2772-2784.

Narendra D. P., Youle R. J. Targeting mitochondrial dysfunction: role for PINK1 and Parkin in mitochondrial quality control. Antioxid. Redox Signal. 2011;14:1929-1938.

Narendra D., Tanaka A., Suen D. F., Youle R. J. Parkin-induced mitophagy in the pathogenesis of Parkinson disease. Autophagy. 2009;5:706-708.

Narendra D. P., Jin S. M., Tanaka A., Suen D. F., Gautier C. A., Shen J., Cookson M. R., Youle R. J. PINK1 is selectively stabilized on impaired mitochondria to activate Parkin. PLoS Biol. 2010;8:e1000298.

Negrette-Guzmán M., Huerta-Yepez S., Tapia E., Pedraza-Chaverri J. Free Radic. Biol. Med. 2013;65:1078-1089.

Novak I., Kirkin V., McEwan D. G., Zhang J., Wild P., Rozenknop A., Rogov V., Löhr F., Popovic D., Occhipinti A. Nix is a selective autophagy receptor for mitochondrial clearance. EMBO Rep. 2010;11:45-51.

Padman B. S., Bach M., Lucarelli G., Prescott M., Ramm G. The protonophore CCCP interferes with lysosomal degradation of autophagic cargo in yeast and mammalian cells. Autophagy. 2013;9:1862-1875.

Pankiv S., Clausen T. H., Lamark T., Brech A., Bruun J. A., Outzen H., Øvervatn A., Bjørkøy G., Johansen T. p62/SQSTM1 binds directly to Atg8/LC3 to facilitate degradation of ubiquitinated protein aggregates by autophagy. J. Biol. Chem. 2007;282:24131-24145.

Pawlyk A. C., Giasson B. I., Sampathu D. M., Perez F. A., Lim K. L., Dawson V. L., Dawson T. M., Palmiter R. D., Trojanowski J. Q., Lee V. M. Novel monoclonal antibodies demonstrate biochemical variation of brain parkin with age. J. Biol. Chem. 2003;278:48120-48128.

Salminen A., Kaarniranta K., Haapasalo A., Hiltunen M., Soininen H., Alafuzoff I. Emerging role of p62/sequestosome-1 in the pathogenesis of Alzheimer's disease. Prog. Neurobiol. 2012;96:87-95.

Scaduto R. C., Jr., Grotyohann L. W. Measurement of mitochondrial membrane potential using fluorescent rhodamine derivatives. Biophys. J. 1999;76:469-477.

Scherz-Shouval R., Elazar Z. Regulation of autophagy by ROS: physiology and pathology. Trends Biochem. Sci. 2011;36:30-38.

Soengas M. S. Mitophagy or how to control the Jekyll and Hyde embedded in mitochondrial metabolism: implications for melanoma progression and drug resistance. Pigment Cell Melanoma Res. 2012;25:721-731. [PubMed]

Stępkowski T. M., Kruszewski M. K. Molecular cross-talk between the NRF2/KEAP1 signaling pathway, autophagy, and apoptosis. Free Radic. Biol. Med. 2011;50:186-1195. [PubMed]

Suski J. M., Lebiedzinska M., Bonora M., Pinton P., Duszynski J., Wieckowski M. R. Relation between mitochondrial membrane potential and ROS formation. Methods Mol. Biol. 2012;810:183-205.

Valente E. M., Abou-Sleiman P. M., Caputo V., Muqit M. M., Harvey K., Gispert S., Ali Z., Del Turco D., Bentivoglio A. R., Healy D. G. Hereditary early-onset Parkinson's disease caused by mutations in PINK1. Science. 2004;304:1158-1160.

Wallace D. C. Mitochondria and cancer. Nat. Rev. Cancer. 2012;12:685-698.

Wang Y., Huang B., Sheng S., Cai M. A novel and efficient synthesis of terminal arylacetylenes via Sonogashira coupling reactions catalysed by MCM-41-supported bidentate phosphine palladium(0) complex. J. Chem. Res. 2007;2007:728-732.

Wooten M. W., Geetha T., Seibenhener M. L., Babu J. R., Diaz-Meco M. T., Moscat J. The p62 scaffold regulates nerve growth factor-induced NF-kappaB activation by influencing TRAF6 polyubiquitination. J. Biol. Chem. 2005;280:35625-35629.

Yoshimori T., Yamamoto A., Moriyama Y., Futai M., Tashiro Y. Bafilomycin A1, a specific inhibitor of vacuolar-type H(+)-ATPase, inhibits acidification and protein degradation in lysosomes of cultured cells. J. Biol. Chem. 1991;266:17707-17712.

Zhu H., Jia Z., Zhang L., Yamamoto M., Misra H. P., Trush M. A., Li Y. Antioxidants and phase 2 enzymes in macrophages: regulation by Nrf2 signaling and protection against oxidative and electrophilic stress. Exp. Biol. Med. (Maywood) 2008;233:463-474.

The invention claimed is:

1. A method for aiding in determining whether a test substance or treatment leads to modification of Keap-1 activity through a non-covalent interaction with Keap-1, the method comprising the steps of:
   providing a cell comprising a level of 18 kDa translocator protein (TSPO);
   exposing a cell to the test substance or treatment;
   measuring TSPO level in the cell after exposure to the test substance or treatment; and
   identifying a test substance or treatment decreasing TSPO level as leading to modification of Keap-1 activity through a non-covalent interaction with Keap-1.

2. The method of claim 1, wherein the cell expresses or comprises PARK2.

3. The method of claim 1, wherein measuring the TSPO level comprises measuring TSPO mRNA.

4. The method of claim 1, wherein measuring the TSPO level comprises measuring TSPO protein.

5. The method of claim 1, wherein measuring the TSPO level comprises measuring TSPO activity.

6. The method of claim 1, wherein the cell is a cell in tissue culture.

7. The method of claim 1, wherein the cell is a mouse embryonic fibroblast cell, a SH-SY5Y cell, a SH-SY5Y cell treated with MPP+, or a Hepa1c1c7 cell.

8. The method of claim 1, wherein the cell is a cell in organ culture, wherein the method comprises assessing the TSPO level in the cell.

9. The method of claim 1, wherein the cell is in a test animal.

10. The method of claim 3 wherein the TSPO mRNA is measured using an RT-PCR method.

11. The method of claim 4 wherein the level of TSPO protein is measured using an immunoquantitation method.

12. The method of claim 5 wherein the level of TSPO activity is measured by measuring mitochondrial cholesterol accumulation.

13. The method of claim 9, wherein the test animal is a mouse or a monkey.

* * * * *